United States Patent
Chen et al.

(10) Patent No.: US 10,006,070 B2
(45) Date of Patent: *Jun. 26, 2018

(54) FUCOSYLATION-DEFICIENT CELLS

(71) Applicant: Regeneron Pharmaceuticals, Inc., Tarrytown, NY (US)

(72) Inventors: Gang Chen, Yorktown Heights, NY (US); Darya Burakov, Yonkers, NY (US); James P. Fandl, LaGrangeville, NY (US)

(73) Assignee: REGENERON PHARMACEUTICALS, INC., Tarrytown, NY (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/378,670

(22) Filed: Dec. 14, 2016

(65) Prior Publication Data

US 2017/0211115 A1  Jul. 27, 2017

Related U.S. Application Data

(60) Continuation of application No. 14/963,178, filed on Dec. 8, 2015, now Pat. No. 9,550,823, which is a division of application No. 13/779,952, filed on Feb. 28, 2013, now Pat. No. 9,206,455, which is a division of application No. 12/791,637, filed on Jun. 1, 2010, now Pat. No. 8,409,838.

(60) Provisional application No. 61/348,858, filed on May 27, 2010, provisional application No. 61/183,400, filed on Jun. 2, 2009.

(51) Int. Cl.
| | |
|---|---|
| *C12N 9/02* | (2006.01) |
| *C12P 21/04* | (2006.01) |
| *C12N 15/00* | (2006.01) |
| *C12N 1/20* | (2006.01) |
| *C07H 21/04* | (2006.01) |
| *C12P 21/00* | (2006.01) |
| *C07K 16/00* | (2006.01) |
| *C07K 16/28* | (2006.01) |
| *C12N 9/04* | (2006.01) |

(52) U.S. Cl.
CPC ............ *C12P 21/005* (2013.01); *C07K 16/00* (2013.01); *C07K 16/2863* (2013.01); *C07K 16/2866* (2013.01); *C12N 9/0006* (2013.01); *C12N 15/00* (2013.01); *C12Y 101/01271* (2013.01); *C07K 2317/14* (2013.01); *C07K 2317/41* (2013.01); *Y02P 20/52* (2015.11)

(58) Field of Classification Search
None
See application file for complete search history.

(56) References Cited

U.S. PATENT DOCUMENTS

| | | |
|---|---|---|
| 7,425,446 B2 | 9/2008 | Kanda et al. |
| 8,329,443 B2 | 12/2012 | Kanda et al. |
| 8,409,838 B2 | 4/2013 | Chen et al. |
| 8,501,914 B2 | 8/2013 | Kanda et al. |
| 8,895,266 B2 | 11/2014 | Kanda et al. |
| 9,206,455 B2 | 12/2015 | Chen et al. |
| 2006/0223147 A1 | 10/2006 | Nishiya et al. |
| 2008/0177043 A1 | 7/2008 | Hanai et al. |
| 2009/0191592 A1 | 7/2009 | Kanda et al. |
| 2010/0304436 A1 | 12/2010 | Chen et al. |
| 2013/0164786 A1 | 6/2013 | Chen et al. |
| 2015/0112046 A1 | 4/2015 | Kanda et al. |
| 2016/0090410 A1 | 3/2016 | Chen et al. |

FOREIGN PATENT DOCUMENTS

| | | |
|---|---|---|
| DE | 600 32 630 T2 | 10/2007 |
| EP | 1 331 266 A1 | 7/2003 |
| EP | 1 443 961 B1 | 5/2009 |
| KR | 10-0877676 | 1/2009 |
| WO | 02/055723 A1 | 7/2002 |
| WO | 03/035835 A2 | 5/2003 |
| WO | 2006/133148 A2 | 12/2006 |
| WO | 2010/141478 A1 | 12/2010 |
| WO | 2012/120500 A2 | 9/2012 |

OTHER PUBLICATIONS

Arnold J.N. et al., "The Impact of Glycosylation on the Biological Function and Structure of Human Immunoglobulins", Annual Reviews Immunol. 25:21-50 (2007).
Becker D.J. et al., Q8K3X2.1, UniProtKB Database (3 pages) (2002).
Becker D.J. et al., "Fucose: Biosynthesis and Biological Function in Mammals", Glycobiology 13(7):41R-53R (Jul. 2003).
Branden C. et al., "Introduction to Protein Structure", Garland Publishing, New York, p. 247 1991).
Iida S. et al., "Nonfucosylated Therapeutic IgG1 Antibody Can Evade the Inhibitory Effect of Serum Immunoglobulin G on Antibody-Dependent Cellular Cytotoxicity Through its High Binding to FcγRIIIa", Clinical Cancer Research 12 (9):2879-2887 (May 1, 2006).
Imai-Nishiya H. et al., "Double Knockdown of α1,6-Fucosyltransferase (FUT8) and GDP-Mannose 4,6-Dehydratase (GMD) in Antibody-Producing Cells: A New Strategy for Generating Fully Non-Fucosylated Therapeutic Antibodies With Enhanced ADCC", BMC Biotechnology 7:84 (2007).

(Continued)

*Primary Examiner* — Yong D Pak
(74) *Attorney, Agent, or Firm* — Scully, Scott, Murphy & Presser, P.C.; Mary Johnson

(57) ABSTRACT

An isolated nucleic acid encoding an FX protein having a serine at position 79, a lysine at position 90, a leucine at position 136, an arginine at position 211, a serine at position 289, and a combination thereof is provided. Cells having a gene encoding a modified FX protein are provided, wherein the cells exhibit a reduced ability to fucosylate a glycoprotein at a first temperature, but exhibit the ability to fucosylate the glycoprotein at a second temperature. Methods and compositions for making glycoproteins with reduced fucosylation are provided.

20 Claims, 16 Drawing Sheets

(56) References Cited

OTHER PUBLICATIONS

Jefferis R., "A Sugar Switch for Anti-Inflammatory Antibodies", Nature Biotechnology 24(10):1230-1231 (Oct. 2006).

Kanda Y. et al., "Comparison of Cell Lines for Stable Production of Fucose-Negative Antibodies With Enhanced ADCC", Biotechnology and Bioengineering 94(4):680-688 (Jul. 2006).

Ma B. et al., "Fucosylation in Prokaryotes and Eukaryotes", Glycobiology 16(12):158R-184R (2006).

Niimmerjahn F. et al., "Agalactosylated IgG Antibodies Depend on Cellular Fc Receptors for In Vivo Activity", PNAS 104(20):8433-8437 (2007).

Niimmerjahn F. et al., "Antibodies, Fc Receptors and Cancer", Current Opinion in Immunology 19(2):239-245 (Apr. 2007).

Noda K. et al., "Relationship Between Elevated FX Expression and Increased Production of GDP-L-Fucose, a Common Donor Substrate for Fucosylation in Human Hepatocellular Carcinoma and Hepatoma Cell Lines", Cancer Research 63(19):6282-6289 (2003).

Ohyama C. et al., "Molecular Cloning and Expression of GDP-D-Mannose-4,6-Dehydratase, a Key Enzyme for Fucose Metabolism Defective in Lec13 Cells", The Journal of Biological Chemistry 273(23):14582-14587 (Jun. 1998).

Patnaik Sic. et al., "Lectin-Resistant CHO Glycosylation Mutants", Methods in Enzymology 416:159-182 (2006).

Shields R.L. et al., "Lack of Fucose on Human IgG1 N-Linked Oligosaccharide Improves Binding to Human FcγRIII and Antibody-Dependent Cellular Toxicity", The Journal of Biological Chemistry 277(30):26733-26740 (Jul. 2002).

Shinkawa T. et al., "The Absence of Fucose But Not the Presence of Galactose or Bisecting N-Acetylglucosamine of Human IgG1 Complex-Type Oligosaccharides Shows the Critical Role of Enhancing Antibody-Dependent Cellular Cytotoxicity", The Journal of Biological Chemistry 278(5):3466-3473 (Jan. 2003).

Smith P.L. et al., "Conditional Control of Selectin Ligand Expression and Global Fucosylation Events in Mice With a Targeted Mutation at the FX Locus", The Journal of Cell Biology 158(4):801-815 (2002).

Sullivan F.X. et al., "Molecular Cloning of Human GDP-Mannose 4,6-Dehydratase and Reconstitution of GDP-Fucose Biosynthesis In Vitro", The Journal of Biological Chemistry 273(14):8193-8202 (Apr. 3, 1998).

Taupin P., "Cell Lines Epxressing Mutant FX Proteins to Generate Proteins With Reduced Rate of Fucosylation" WO2010/141478, Expert Opinion on Therapeutic Patents 21(7):1143-1146 (2011).

Teylaert B. et al., "Molecular Cloning, Characterization, Genomic Organization and Promoter Analysis of the a 1,6-Fucosyltransferase Gene (Fut8) Expressed in the Rat Hybridoma Cell Line YB2/0", BMC Biotechnology 11(1):1-18 (2011).

Tonetti M. et al., "Synthesis of GDP-L-Fucose by the Human FX Protein", The Journal of Biological Chemistry 271(44):27274-27279 (Nov. 1996).

Yamane-Ohnuki N. et al., "Production of Therapeutic Antibodies With Controlled Fucosylation", mABS 1(3)230-236 (May/Jun. 2009).

Australian Examination Report dated May 20, 2015 received in Australian Application No. 2014200152.

International Search Report dated Aug. 5, 2010 received in International Application No. PCT/US2010/036914.

Written Opinion of the International Searching Authority dated Aug. 5, 2010 received in International Application No. PCT/US2010/036914.

International Preliminary Report on Patentability dated Dec. 6, 2011 received in International Application No. PCT/US2010/036914.

"Tissue Specific Transplantation Antigen P35B [Rattus Norvegicus]", GenBank Accession No. NP_001120927.1 (1 page) (May 20, 2008).

Indian Examination Report dated Nov. 10, 2017 received in Indian Patent Application No. 9736/DELNP/2011, together with an English-language translation.

FIG. 1

| | Glycan Form | % Antibody | | | | Glycan Formula | Glycan Structure |
|---|---|---|---|---|---|---|---|
| | | Ab 3.1 | | Ab 3.2 | | | |
| | | No Fucose | 10 mM Fucose | No Fucose | 10 mM Fucose | | |
| Non-Fucosylation | G0 | 45.73 | 2.12 | 32.12 | 1.48 | (GlcNAc)$_2$(Man)$_3$(GlcNAc)$_2$ | |
| | G1 | 43.93 | 2.26 | 49.53 | 2.29 | (GlcNAc)$_2$(Man)$_3$(GlcNAc)$_2$(Gal)$_1$ | |
| | G2 | 8.88 | 0.40 | 12.69 | 0.61 | (GlcNAc)$_2$(Man)$_3$(GlcNAc)$_2$(Gal)$_2$ | |
| Fucosylation | G0 | 0.43 | 30.2 | 1.45 | 17.48 | Fuc(GlcNAc)$_2$(Man)$_3$(GlcNAc)$_2$ | |
| | G1 | 0.54 | 51.24 | 2.01 | 57.74 | Fuc(GlcNAc)$_2$(Man)$_3$(GlcNAc)$_2$(Gal)$_1$ | |
| | G2 | 0.50 | 13.78 | 2.27 | 20.41 | Fuc(GlcNAc)$_2$(Man)$_3$(GlcNAc)$_2$(Gal)$_2$ | |

FIG. 16

SEQUENCE LISTING

```
<160> NUMBER OF SEQ ID NOS: 14

<210> SEQ ID NO 1
<211> LENGTH: 321
<212> TYPE: PRT
<213> ORGANISM: Cricetulus griseus

<400> SEQUENCE: 1

Met Gly Glu Pro Gln Gly Ser Arg Arg Ile Leu Val Thr Gly Gly Ser
1               5                   10                  15

Gly Leu Val Gly Arg Ala Ile Gln Lys Val Val Ala Asp Gly Ala Gly
            20                  25                  30

Leu Pro Gly Glu Glu Trp Val Phe Val Ser Ser Lys Asp Ala Asp Leu
        35                  40                  45

Thr Asp Ala Ala Gln Thr Gln Ala Leu Phe Gln Lys Val Gln Pro Thr
    50                  55                  60

His Val Ile His Leu Ala Ala Met Val Gly Gly Leu Phe Arg Asn Ile
65                  70                  75                  80

Lys Tyr Asn Leu Asp Phe Trp Arg Lys Asn Val His Ile Asn Asp Asn
                85                  90                  95

Val Leu His Ser Ala Phe Glu Val Gly Thr Arg Lys Val Val Ser Cys
            100                 105                 110

Leu Ser Thr Cys Ile Phe Pro Asp Lys Thr Thr Tyr Pro Ile Asp Glu
        115                 120                 125

Thr Met Ile His Asn Gly Pro Pro His Ser Ser Asn Phe Gly Tyr Ser
    130                 135                 140

Tyr Ala Lys Arg Met Ile Asp Val Gln Asn Arg Ala Tyr Phe Gln Gln
145                 150                 155                 160

His Gly Cys Thr Phe Thr Ala Val Ile Pro Thr Asn Val Phe Gly Pro
                165                 170                 175

His Asp Asn Phe Asn Ile Glu Asp Gly His Val Leu Pro Gly Leu Ile
            180                 185                 190

His Lys Val His Leu Ala Lys Ser Asn Gly Ser Ala Leu Thr Val Trp
        195                 200                 205

Gly Thr Gly Lys Pro Arg Arg Gln Phe Ile Tyr Ser Leu Asp Leu Ala
    210                 215                 220

Arg Leu Phe Ile Trp Val Leu Arg Glu Tyr Asn Glu Val Glu Pro Ile
225                 230                 235                 240

Ile Leu Ser Val Gly Glu Glu Asp Glu Val Ser Ile Lys Glu Ala Ala
                245                 250                 255

Glu Ala Val Val Glu Ala Met Asp Phe Cys Gly Glu Val Thr Phe Asp
            260                 265                 270

Ser Thr Lys Ser Asp Gly Gln Tyr Lys Lys Thr Ala Ser Asn Gly Lys
        275                 280                 285

Leu Arg Ala Tyr Leu Pro Asp Phe Arg Phe Thr Pro Phe Lys Gln Ala
    290                 295                 300
```

```
Val Lys Glu Thr Cys Ala Trp Phe Thr Asp Asn Tyr Glu Gln Ala Arg
305                 310                 315                 320

Lys
```

<210> SEQ ID NO 2
<211> LENGTH: 321
<212> TYPE: PRT
<213> ORGANISM: Artificial Sequence
<220> FEATURE:
<223> OTHER INFORMATION: synthetic

<400> SEQUENCE: 2

```
Met Gly Glu Pro Gln Gly Ser Arg Arg Ile Leu Val Thr Gly Gly Ser
  1               5                  10                  15

Gly Leu Val Gly Arg Ala Ile Gln Lys Val Val Ala Asp Gly Ala Gly
             20                  25                  30

Leu Pro Gly Glu Glu Trp Val Phe Val Ser Ser Lys Asp Ala Asp Leu
         35                  40                  45

Thr Asp Ala Ala Gln Thr Gln Ala Leu Phe Gln Lys Val Gln Pro Thr
 50                  55                  60

His Val Ile His Leu Ala Ala Met Val Gly Gly Leu Phe Arg Asn Ile
 65                  70                  75                  80

Lys Tyr Asn Leu Asp Phe Trp Arg Lys Val His Ile Asn Asp Asn
                 85                  90                  95

Val Leu His Ser Ala Phe Glu Val Gly Thr Arg Lys Val Val Ser Cys
                100                 105                 110

Leu Ser Thr Cys Ile Phe Pro Asp Lys Thr Thr Tyr Pro Ile Asp Glu
            115                 120                 125

Thr Met Ile His Asn Gly Pro Pro His Ser Ser Asn Phe Gly Tyr Ser
130                 135                 140

Tyr Ala Lys Arg Met Ile Asp Val Gln Asn Arg Ala Tyr Phe Gln Gln
145                 150                 155                 160

His Gly Cys Thr Phe Thr Ala Val Ile Pro Thr Asn Val Phe Gly Pro
                165                 170                 175

His Asp Asn Phe Asn Ile Glu Asp Gly His Val Leu Pro Gly Leu Ile
            180                 185                 190

His Lys Val His Leu Ala Lys Ser Asn Gly Ser Ala Leu Thr Val Trp
        195                 200                 205

Gly Thr Gly Lys Pro Arg Arg Gln Phe Ile Tyr Ser Leu Asp Leu Ala
210                 215                 220

Arg Leu Phe Ile Trp Val Leu Arg Glu Tyr Asn Glu Val Glu Pro Ile
225                 230                 235                 240

Ile Leu Ser Val Gly Glu Glu Asp Glu Val Ser Ile Lys Glu Ala Ala
                245                 250                 255

Glu Ala Val Val Glu Ala Met Asp Phe Cys Gly Glu Val Thr Phe Asp
            260                 265                 270

Ser Thr Lys Ser Asp Gly Gln Tyr Lys Lys Thr Ala Ser Asn Gly Lys
        275                 280                 285

Ser Arg Ala Tyr Leu Pro Asp Phe Arg Phe Thr Pro Phe Lys Gln Ala
290                 295                 300

Val Lys Glu Thr Cys Ala Trp Phe Thr Asp Asn Tyr Glu Gln Ala Arg
305                 310                 315                 320

Lys
```

<210> SEQ ID NO 3

```
<211> LENGTH: 321
<212> TYPE: PRT
<213> ORGANISM: Macacca mulatta

<400> SEQUENCE: 3

Met Gly Glu Pro Gln Gly Ser Met Arg Ile Leu Val Thr Gly Gly Ser
 1               5                  10                  15

Gly Leu Val Gly Lys Ala Ile Gln Lys Val Val Ala Asp Gly Ala Gly
            20                  25                  30

Leu Pro Gly Glu Asp Trp Val Phe Val Ser Ser Lys Asp Ala Asp Leu
        35                  40                  45

Thr Asp Ala Ala Gln Thr Arg Ala Leu Phe Glu Lys Val Arg Pro Thr
50                  55                  60

His Val Ile His Leu Ala Ala Met Val Gly Gly Leu Phe Arg Asn Ile
65                  70                  75                  80

Lys Tyr Asn Leu Asp Phe Trp Arg Lys Asn Val His Ile Asn Asp Asn
                85                  90                  95

Val Leu His Ser Ala Phe Glu Val Gly Ala Cys Lys Val Val Ser Cys
            100                 105                 110

Leu Ser Thr Cys Ile Phe Pro Asp Lys Thr Thr Tyr Pro Ile Asp Glu
        115                 120                 125

Thr Met Ile His Asn Gly Pro Pro His Ser Ser Asn Phe Gly Tyr Ser
130                 135                 140

Tyr Ala Lys Arg Met Ile Asp Val Gln Asn Arg Ala Tyr Phe Gln Gln
145                 150                 155                 160

Tyr Gly Cys Thr Phe Thr Ala Val Ile Pro Thr Asn Val Phe Gly Pro
                165                 170                 175

His Asp Asn Phe Asn Ile Glu Asp Gly His Val Leu Pro Gly Leu Ile
            180                 185                 190

His Lys Val His Leu Ala Lys Ser Ser Ser Ala Leu Thr Val Trp
        195                 200                 205

Gly Thr Gly Lys Pro Arg Arg Gln Phe Ile Tyr Ser Leu Asp Leu Ala
210                 215                 220

Gln Leu Phe Ile Trp Val Leu Arg Glu Tyr Asn Glu Val Glu Pro Ile
225                 230                 235                 240

Ile Leu Ser Val Gly Glu Glu Asp Glu Val Ser Ile Lys Glu Ala Ala
                245                 250                 255

Glu Ala Val Val Glu Ala Met Asp Phe His Gly Glu Val Thr Phe Asp
            260                 265                 270

Thr Ser Lys Ser Asp Gly Gln Phe Lys Lys Thr Ala Ser Asn Ser Lys
        275                 280                 285

Leu Arg Thr Tyr Leu Pro Asp Phe Arg Phe Thr Pro Phe Lys Gln Ala
    290                 295                 300

Val Lys Glu Thr Cys Ala Trp Phe Thr Asp Asn Tyr Glu Gln Ala Arg
305                 310                 315                 320

Lys

<210> SEQ ID NO 4
<211> LENGTH: 321
<212> TYPE: PRT
<213> ORGANISM: Homo sapiens

<400> SEQUENCE: 4

Met Gly Glu Pro Gln Gly Ser Met Arg Ile Leu Val Thr Gly Gly Ser
 1               5                  10                  15
```

Gly Leu Val Gly Lys Ala Ile Gln Lys Val Val Ala Asp Gly Ala Gly
                20                  25                  30

Leu Pro Gly Glu Asp Trp Val Phe Val Ser Ser Lys Asp Ala Asp Leu
            35                  40                  45

Thr Asp Thr Ala Gln Thr Arg Ala Leu Phe Glu Lys Val Gln Pro Thr
    50                  55                  60

His Val Ile His Leu Ala Ala Met Val Gly Gly Leu Phe Arg Asn Ile
65                  70                  75                  80

Lys Tyr Asn Leu Asp Phe Trp Arg Lys Asn Val His Met Asn Asp Asn
                85                  90                  95

Val Leu His Ser Ala Phe Glu Val Gly Ala Arg Lys Val Ser Cys
            100                 105                 110

Leu Ser Thr Cys Ile Phe Pro Asp Lys Thr Thr Tyr Pro Ile Asp Glu
        115                 120                 125

Thr Met Ile His Asn Gly Pro Pro His Asn Ser Asn Phe Gly Tyr Ser
    130                 135                 140

Tyr Ala Lys Arg Met Ile Asp Val Gln Asn Arg Ala Tyr Phe Gln Gln
145                 150                 155                 160

Tyr Gly Cys Thr Phe Thr Ala Val Ile Pro Thr Asn Val Phe Gly Pro
                165                 170                 175

His Asp Asn Phe Asn Ile Glu Asp Gly His Val Leu Pro Gly Leu Ile
            180                 185                 190

His Lys Val His Leu Ala Lys Ser Gly Ser Ala Leu Thr Val Trp
        195                 200                 205

Gly Thr Gly Asn Pro Arg Arg Gln Phe Ile Tyr Ser Leu Asp Leu Ala
    210                 215                 220

Gln Leu Phe Ile Trp Val Leu Arg Glu Tyr Asn Glu Val Glu Pro Ile
225                 230                 235                 240

Ile Leu Ser Val Gly Glu Glu Asp Glu Val Ser Ile Lys Glu Ala Ala
                245                 250                 255

Glu Ala Val Val Glu Ala Met Asp Phe His Gly Glu Val Thr Phe Asp
            260                 265                 270

Thr Thr Lys Ser Asp Gly Gln Phe Lys Lys Thr Ala Ser Asn Ser Lys
        275                 280                 285

Leu Arg Thr Tyr Leu Pro Asp Phe Arg Phe Thr Pro Phe Lys Gln Ala
    290                 295                 300

Val Lys Glu Thr Cys Ala Trp Phe Thr Asp Asn Tyr Glu Gln Ala Arg
305                 310                 315                 320

Lys

<210> SEQ ID NO 5
<211> LENGTH: 321
<212> TYPE: PRT
<213> ORGANISM: Mus musculus

<400> SEQUENCE: 5

Met Gly Glu Pro His Gly Ser Met Arg Ile Leu Val Thr Gly Gly Ser
 1               5                  10                  15

Gly Leu Val Gly Arg Ala Ile Gln Lys Val Val Ala Asp Gly Ala Gly
                20                  25                  30

Leu Pro Gly Glu Glu Trp Val Phe Val Ser Ser Lys Asp Ala Asp Leu
            35                  40                  45

Thr Asp Ala Ala Gln Thr Gln Ala Leu Phe Gln Lys Val Gln Pro Thr
    50                  55                  60

His Val Ile His Leu Ala Ala Met Val Gly Gly Leu Phe Arg Asn Ile
65                  70                  75                  80

Lys Tyr Asn Leu Asp Phe Trp Arg Lys Asn Val His Ile Asn Asp Asn
                85                  90                  95

Val Leu His Ser Ala Phe Glu Val Gly Ala Arg Lys Val Val Ser Cys
            100                 105                 110

Leu Ser Thr Cys Ile Phe Pro Asp Lys Thr Thr Tyr Pro Ile Asp Glu
        115                 120                 125

Thr Met Ile His Asn Gly Pro Pro His Ser Ser Asn Phe Gly Tyr Ser
    130                 135                 140

Tyr Ala Lys Arg Met Ile Asp Val Gln Asn Arg Ala Tyr Phe Gln Gln
145                 150                 155                 160

His Gly Cys Thr Phe Thr Ala Val Ile Pro Thr Asn Val Phe Gly Pro
                165                 170                 175

Tyr Asp Asn Phe Asn Ile Glu Asp Gly His Val Leu Pro Gly Leu Ile
            180                 185                 190

His Lys Val His Leu Ala Lys Ser Ser Asp Ser Ala Leu Thr Val Trp
        195                 200                 205

Gly Thr Gly Lys Pro Arg Arg Gln Phe Ile Tyr Ser Leu Asp Leu Ala
    210                 215                 220

Arg Leu Phe Ile Trp Val Leu Arg Glu Tyr Ser Glu Val Glu Pro Ile
225                 230                 235                 240

Ile Leu Ser Val Gly Glu Glu Asp Glu Val Ser Ile Lys Glu Ala Ala
                245                 250                 255

Glu Ala Val Val Glu Ala Met Asp Phe Asn Gly Glu Val Thr Phe Asp
            260                 265                 270

Ser Thr Lys Ser Asp Gly Gln Tyr Lys Lys Thr Ala Ser Asn Gly Lys
        275                 280                 285

Leu Arg Ser Tyr Leu Pro Asp Phe Arg Phe Thr Pro Phe Lys Gln Ala
    290                 295                 300

Val Lys Glu Thr Cys Thr Trp Phe Thr Asp Asn Tyr Glu Gln Ala Arg
305                 310                 315                 320

Lys

<210> SEQ ID NO 6
<211> LENGTH: 321
<212> TYPE: PRT
<213> ORGANISM: Rattus norvegicus

<400> SEQUENCE: 6

Met Gly Glu Pro His Gly Ser Met Arg Ile Leu Val Thr Gly Gly Ser
1               5                   10                  15

Gly Leu Val Gly Arg Ala Ile Gln Lys Val Val Ala Asp Gly Ala Gly
            20                  25                  30

Leu Pro Gly Glu Glu Trp Val Phe Val Ser Ser Lys Asp Ala Asp Leu
        35                  40                  45

Thr Asp Ala Ala Gln Thr Gln Ala Leu Phe Gln Lys Val Gln Pro Thr
    50                  55                  60

His Val Ile His Leu Ala Ala Met Val Gly Gly Leu Phe Arg Asn Ile
65                  70                  75                  80

Lys Tyr Asn Leu Asp Phe Trp Arg Lys Asn Val His Ile Asn Asp Asn
                85                  90                  95

Val Leu His Ser Ala Phe Glu Val Gly Thr Arg Lys Val Val Ser Cys
            100                 105                 110

```
Leu Ser Thr Cys Ile Phe Pro Asp Lys Thr Thr Tyr Pro Ile Asp Glu
        115                 120                 125

Thr Met Ile His Asn Gly Pro Pro His Ser Ser Asn Phe Gly Tyr Ser
    130                 135                 140

Tyr Ala Lys Arg Met Ile Asp Val Gln Asn Arg Ala Tyr Phe Gln Gln
145                 150                 155                 160

His Gly Cys Thr Phe Thr Ser Val Ile Pro Thr Asn Val Phe Gly Pro
            165                 170                 175

Tyr Asp Asn Phe Asn Ile Glu Asp Gly His Val Leu Pro Gly Leu Ile
            180                 185                 190

His Lys Val His Leu Ala Lys Ser Ser Gly Ser Ala Leu Thr Val Trp
        195                 200                 205

Gly Thr Gly Lys Pro Arg Arg Gln Phe Ile Tyr Ser Leu Asp Leu Ala
    210                 215                 220

Arg Leu Phe Ile Trp Val Leu Arg Glu Tyr Asn Glu Val Glu Pro Ile
225                 230                 235                 240

Ile Leu Ser Val Gly Glu Glu Asp Glu Val Ser Ile Lys Glu Ala Ala
            245                 250                 255

Glu Ala Val Val Glu Ala Met Asp Phe Ser Gly Glu Val Thr Phe Asp
            260                 265                 270

Ser Thr Lys Ser Asp Gly Gln Tyr Lys Lys Thr Ala Ser Asn Gly Lys
        275                 280                 285

Leu Arg Ser Tyr Leu Pro Asp Phe Cys Phe Thr Pro Phe Lys Gln Ala
    290                 295                 300

Val Lys Glu Thr Cys Ala Trp Phe Thr Glu Asn Tyr Glu Gln Ala Arg
305                 310                 315                 320

Lys

<210> SEQ ID NO 7
<211> LENGTH: 22
<212> TYPE: DNA
<213> ORGANISM: Artificial Sequence
<220> FEATURE:
<223> OTHER INFORMATION: synthetic

<400> SEQUENCE: 7
ctacaatctt ggtgcccaga gc                                          22

<210> SEQ ID NO 8
<211> LENGTH: 21
<212> TYPE: DNA
<213> ORGANISM: Artificial Sequence
<220> FEATURE:
<223> OTHER INFORMATION: synthetic

<400> SEQUENCE: 8
tccagttcag tttctgctgc g                                           21

<210> SEQ ID NO 9
<211> LENGTH: 23
<212> TYPE: DNA
<213> ORGANISM: Artificial Sequence
<220> FEATURE:
<223> OTHER INFORMATION: synthetic

<400> SEQUENCE: 9
ttccctgaca agaccaccta tcc                                         23

<210> SEQ ID NO 10
```

```
<211> LENGTH: 22
<212> TYPE: DNA
<213> ORGANISM: Artificial Sequence
<220> FEATURE:
<223> OTHER INFORMATION: synthetic

<400> SEQUENCE: 10
tagttgtcgg tgaaccaggc ac                                              22

<210> SEQ ID NO 11
<211> LENGTH: 22
<212> TYPE: DNA
<213> ORGANISM: Artificial Sequence
<220> FEATURE:
<223> OTHER INFORMATION: synthetic

<400> SEQUENCE: 11
gatgaggaca gcaggaacaa gc                                              22

<210> SEQ ID NO 12
<211> LENGTH: 23
<212> TYPE: DNA
<213> ORGANISM: Artificial Sequence
<220> FEATURE:
<223> OTHER INFORMATION: synthetic

<400> SEQUENCE: 12
agcactcttc tcaccctctt tgg                                             23

<210> SEQ ID NO 13
<211> LENGTH: 24
<212> TYPE: DNA
<213> ORGANISM: Artificial Sequence
<220> FEATURE:
<223> OTHER INFORMATION: synthetic

<400> SEQUENCE: 13
agccaagggt aagtaaggag gacg                                            24

<210> SEQ ID NO 14
<211> LENGTH: 22
<212> TYPE: DNA
<213> ORGANISM: Artificial Sequence
<220> FEATURE:
<223> OTHER INFORMATION: synthetic

<400> SEQUENCE: 14
ttgtagacag cctccatcct cg                                              22
```

FUCOSYLATION-DEFICIENT CELLS

CROSS-REFERENCE TO RELATED APPLICATIONS

This application is a continuation application of U.S. Ser. No. 14/963,178 filed Dec. 8, 2015, which is a divisional application of U.S. Ser. No. 13/779,952 filed Feb. 28, 2013 now U.S. Pat. No. 9,206,455, which is a divisional application of U.S. Ser. No. 12/791,637 filed Jun. 1, 2010 now U.S. Pat. No. 8,409,838, which claims the benefit under 35 USC Section 119(e) of U.S. Provisional Application Ser. No. 61/183,400 filed Jun. 2, 2009, and U.S. Provisional Application Ser. No. 61/348,858, filed May 27, 2010, each of which applications is hereby incorporated by reference.

REFERENCE TO A SEQUENCE LISTING AS A TEXT FILE VIA EFS WEB

This application includes a sequence listing submitted herewith as a text file named 471511_SEQLST.txt created on Dec. 8, 2015, and containing 17,981 bytes. The material contained in this text file is incorporated by reference in its entirety for all purposes.

FIELD

The invention relates to a modified mammalian enzyme in the fucosylation pathway, wherein cells bearing the modified mammalian enzyme exhibit a reduced ability to fucosylate a protein, and to cells comprising a genetic modification that results in a reduced ability to fucosylate a protein. The invention includes mammalian cell lines (e.g., CHO lines) that express proteins, including antibodies, with reduced fucosylation as compared to wild-type cell lines. The invention also relates to conditional control of protein fucosylation.

BACKGROUND

Cell lines that are unable to fucosylate proteins are known in the art. A number of loss-of-function mutants that are unable to fucosylate proteins are known, perhaps most notably certain Chinese hamster ovary (CHO) cell mutants selected for resistance to certain lectins. Such cell lines are isolated by repeated selection for the inability to bind a particular lectin, e.g., the *Lens culinaris* lectin, in the presence of a mutagen. Other cell lines reportedly incapable of fucosylating proteins, e.g., antibodies, are known, see, e.g., U.S. Pat. No. 7,425,466 and U.S. Pat. No. 7,214,775 (α1,6-fucosyltransferase, i.e., FUT8 mutant). There remains a need in the art for cell lines with reduced ability to fucosylate proteins, in particular for cells with reduced fucosylation ability in the absence of a knockout, and for cells that conditionally fucosylate proteins.

SUMMARY

In one aspect, an isolated modified GDP-4-keto-6-deoxymannose-3,5-epimerase-4-reductase (FX) protein is provided, comprising a modification selected from the group consisting of 79S, 90K, 136L, 211R, 289S, and a combination thereof. In one embodiment, the FX protein comprises a 289S modification. In one embodiment, the FX protein comprises a 289S modification and at least one modification selected from the group consisting of 79S, 90K, 136L, 211R, and a combination thereof.

In one aspect, a nucleic acid that codes for a modified FX protein sequence is provided. In a specific embodiment, the nucleic acid is a cDNA. In one embodiment, an expression vector or a targeting vector comprising the nucleic acid is provided. In one embodiment, the nucleic acid of the targeting vector comprises an intron. In one embodiment, the nucleic acid of the targeting vector comprises a cDNA encoding the modified FX protein. In a specific embodiment, the targeting vector comprises a targeting sequence that targets the vector to a locus in a human, non-human primate, hamster, mouse, or rat genome.

In one aspect, a cell is provided that comprises a modification to a nucleic acid that codes for an FX protein, or that expresses an FX protein with a modification, wherein the cell does not express or does not substantially express a wild-type FX protein. In a specific embodiment, the cell exhibits no more than 10%, no more than 5%, no more than 2%, or no more than 1% wild-type FX protein as compared with a cell that lacks the modification.

In one embodiment, the cell comprising the modified FX protein or nucleic acid expresses an Fc-containing glycoprotein, wherein the cell fucosylates no more than 90%, no more than 95%, no more than 96%, no more than 97%, no more than 98%, or no more than 99% of the glycoprotein as compared with a cell that lacks the modification.

In one aspect, a cell is provided that comprises a modification to a nucleic acid that encodes an FX protein, or that expresses an FX protein with a modification, wherein the cell lacks or substantially lacks the ability to fucosylate a glycoprotein at a first temperature, but does not lack or does not substantially lack the ability to fucosylate the glycoprotein at a second temperature.

In one embodiment, the first temperature is about 37° C. In one embodiment, the second temperature is about 34° C.

In one embodiment, the ability to fucosylate the glycoprotein at the first temperature is about 1% to about 10% of the ability to fucosylate the glycoprotein exhibited by a cell that lacks the modification. In one embodiment, the ability to fucosylate the glycoprotein at the second temperature is about 70%, 80%, 90%, or more as compared with the ability to fucosylate the glycoprotein by a cell that lacks the modification.

In a specific embodiment, the FX protein modification comprises an amino acid substitution selected from the group consisting of the following amino acid substitutions: 90K, 289S, 211R, 136L, 79S, and a combination thereof. In a specific embodiment, the substitution is 289S.

In one embodiment, the FX protein is from a nonhuman primate (e.g., *Macaca mulatta*), a human, a mouse (e.g., *Mus musculus*), a rat (e.g., *Rattus norvegicus*), or a hamster (e.g., Chinese hamster, or *Cricetulus griseus*). In a specific embodiment, the FX protein comprises the amino acid sequence of SEQ ID NO:1, SEQ ID NO:3, SEQ ID NO:4, SEQ ID NO:5, or SEQ ID NO:6, and bears one or more modifications (e.g., amino acid substitutions) as described herein.

In one embodiment, the nucleic acid codes for a FX protein that is at least 90% or at least 95% identical to the sequence of SEQ ID NO:1, and further comprises one or more of the following amino acids at one or more of the following positions: 79S, 90K, 136L, 211R, and 289S.

In one embodiment, the nucleic acid codes for a FX that is at least 95% identical to the FX of SEQ ID NO:2. In a specific embodiment, the FX has the amino acid sequence of SEQ ID NO:2.

In one aspect, a cell is provided, wherein the cell comprises a modification that results in a reduced ability of the cell to fucosylate a glycoprotein, and the modification comprises a mutation or alteration in the sequence of a FX gene that results in the reduced ability to fucosylate the glycoprotein.

In one embodiment, the cell expresses a wild-type fucosylation pathway enzyme selected from the group consisting of GDP-mannose 4,6-dehydratase (GMD), a wild-type GDP-β-L-fucose pyrophosphorylase (GFPP), a wild-type α-1,6-fucolysltransferase (FUT8), and a combination thereof.

In one aspect, a mammalian cell capable of fucosylating a protein is provided, wherein the cell comprises a modification in a FX gene, wherein the modification results in at least a 90% reduction in the cell's ability to fucosylate a protein in comparison to a cell that lacks the mutation or alteration.

In one embodiment, the reduction is about 90%, 91%, 92%, 93%, 94%, 95%, 96%, 97%, 98%, or 99% in comparison with a mammalian cell that does not contain the modification.

In one embodiment, comparison of a modified cell according to the invention and a cell that does not comprise the modification is conducted under the same or under essentially the same conditions (e.g., media, temperature, cell density, etc.).

In one embodiment, the cell is selected from a COS, CHO, 293, BHK, HeLa, Vero, a mammalian transfected with adenovirus genes, e.g., AD5 E1, including but not limited to an immortalized human retinal cell transfected with an adenovirus gene, e.g., a PER.C6™ cell, and an NSO cell. In one embodiment, the cell is a Chinese hamster ovary (CHO) cell. In a specific embodiment, the CHO cell is a CHO K1 cell.

In one embodiment, the modification is selected from the group consisting of the following amino acids: 79S, 90K, 136L, 211R, 289S, and a combination thereof. In a specific embodiment, the substitution comprises 289S. In another specific embodiment, the substitution comprises 289S and one or more of 79S, 90K, 136L, and 211R.

In one embodiment, the cell comprises an FX gene that encodes a protein comprising the sequence of SEQ ID NO:1, with one or more amino acid substitutions selected from the group consisting of N79S, N90K, P136L, G211R, L289S, and a combination thereof. In a specific embodiment, the amino acid substitution comprises L289S and one or more of N79S, N90K, P136L, and G211R.

In one embodiment, the cell further comprises at least one nucleic acid encoding an immunoglobulin protein. In a specific embodiment, the immunoglobulin protein is a human protein or a mouse protein. In a specific embodiment, the immunoglobulin protein comprises an immunoglobulin light chain. In a specific embodiment, the immunoglobulin protein comprises an immunoglobulin heavy chain. In one embodiment, the immunoglobulin heavy chain is of an IgG1, IgG2, IgG3, or IgG4 isotype. In one embodiment, the immunoglobulin heavy chain is an IgG1 isotype, e.g., a human IgG1 isotype. In one embodiment, the variable region of the heavy and/or light chain comprises a human CDR, in another embodiment a mouse CDR, in another embodiment a humanized CDR of a mouse or a non-human primate.

In one embodiment, the cell comprises a nucleic acid encoding a CH2 and a CH3 domain of an immunoglobulin heavy chain. In one embodiment, the immunoglobulin heavy chain is of an isotype IgG1, IgG2, IgG3, or IgG4.

In one embodiment, the protein is an antigen-binding protein. In a specific embodiment, the antigen-binding protein is an antibody. In specific embodiments, the antibody comprises a heavy chain of an IgA, IgD, IgE, IgG, or IgM isotype. In one embodiment, the antigen-binding protein is an antibody of IgG1 isotype.

In one embodiment, the protein is an antibody and only about 5%, 4%, 3%, 2%, 1%, or 0.5% of the antibody protein made by the cell is fucosylated. In one embodiment, the amount of antibody protein made that is fucosylated is measured by overnight deglycosylation of antibody protein with PNGase F followed by oligosaccharide analysis via HPLC wherein fucosyl-containing oligosaccharides are quantified by integration of glycan peak area, and, e.g., protein fucosylation is calculated based on glycan peak area. In a specific embodiment, fucosylated glycans are identified by mass spectroscopy.

In one aspect, a method for making an antigen-binding protein is provided, the method comprising: (a) providing a cell capable of fucosylating a protein, wherein the cell comprises a modification in a FX gene that results in at least a 90% reduction in the cell's capability to fucosylate a protein; (b) introducing into the cell a nucleic acid sequence encoding an antigen-binding protein; (c) maintaining the cell under conditions sufficient to express the nucleic acid sequence to produce the antigen-binding protein; and, (d) recovering the antigen-binding protein expressed by the cell.

In one embodiment, the antigen-binding protein is an antibody. In a specific embodiment, the antibody is selected from a human antibody, a mouse antibody, a chimeric human/mouse antibody, and a non-human primate antibody.

In one embodiment, the cell is a Chinese hamster ovary (CHO) cell.

In one embodiment, the reduction in the cell's capacity to fucosylate a protein is 91%, 92%, 93%, 94%, 95%, 96%, 97%, 98%, 99%, or 99.5% as compared to a cell that lacks the modification in the FX gene.

In one embodiment, the modification is selected from the group consisting of the following amino acids at the following positions: 79S, 90K, 136L, 211R, and 289S. In one embodiment, the modification comprises 289S and at least one of 79S, 90K, 136L, and 211R.

In one embodiment, the fucosyltransferase gene encodes a protein comprising the sequence of SEQ ID NO:1, with amino acid substitutions selected from the group consisting of N79S, N90K, P136L, G211R, and L289S. In one embodiment the modification comprises L289S and at least one of N79S, N90K, P136L, and G211R.

In one embodiment, the antibody or fragment thereof is a human antibody or fragment thereof. In a specific embodiment, the antibody is an IgG1 isotype, e.g., a human IgG1.

In one embodiment, the recovered antibody has no more that about 5% fucosylation as compared to the same antibody made in a wild-type cell that lacks the modification, in another embodiment, no more than 4%, 3%, 2%, 1%, or 0.5% fucosylation as compared to the same antibody made in a wild-type cell that lacks the modification.

In one aspect, a cell is provided that expresses a wild-type fucosylation pathway enzyme selected from the group consisting of GDP-mannose 4,6-dehydratase (GMD), a wild-type GDP-β-L-fucose pyrophosphorylase (GFPP), a wild-type αx-1,6-fucolysltransferase (FUT8), and a combination thereof; wherein the cell comprises a modified FX gene, wherein the cell has a reduced ability to fucosylate a glycoprotein as compared to a cell that lacks the modification to the FX gene.

In a specific embodiment, the glycoprotein comprises an Fc. In one embodiment, the protein is an antibody. In one embodiment, the protein comprises a sequence of an IgG. In a specific embodiment, the sequence of an IgG is an IgG1, an IgG2, an IgG3, an IgG4 sequence, or a combination thereof. In a specific embodiment, the protein is an antibody and the antibody comprises an Fc having an IgG1, IgG2, IgG3, and/or IgG4 sequence.

In one embodiment, the cell is selected from CHO, COS, human retinal (e.g., PER.C6™), Vero, or HeLa cell.

In one aspect, a method is provided for making a glycoprotein, comprising expressing a glycoprotein in a mammalian cell, wherein the mammalian cell comprises a modified FX gene.

In one embodiment, a method for making a glycoprotein is provided, comprising culturing a glycoprotein-expressing CHO cell in culture medium under conditions sufficient for the CHO cell to express the glycoprotein, and recovering from the CHO cell or the culture medium the expressed glycoprotein. In one embodiment, the expressed glycoprotein is no more than about 5% fucosylated. In one embodiment, no more than about 4%, 3%, 2%, 1%, or 0.5% fucosylated. In a specific embodiment, the percent fucosylation is a mole percent of fucose to glycan. In a specific embodiment, the percent fucosylation is a mole percent of fucose to glycoprotein. In a specific embodiment, the molar ratio of nonfucosylated to fucosylated protein is about 0.90 to 0.10, about 0.91 to 0.09, about 0.92 to 0.08, about 0.93 to 0.07, about 0.94 to 0.06, about 0.95 to 0.05, about 0.96 to 0.04, about 0.97 to 0.03, about 0.98 to 0.02, or about 0.99 to 0.01.

In one embodiment, the glycoprotein comprises an immunoglobulin CH2 and CH3 region having at position 297 (EU numbering) the following glycan moiety: GlcNAc(1) bound to the glycoprotein through the N-linkage; GlcNAc(1)-GlcNAc(2)-Mannose(1), wherein Mannose(1) bears a first and a second moiety, wherein the first moiety consists essentially of Mannose(2)-ManGlcNAc(3); and wherein the second moiety consists essentially of Mannose(3)-GlcNAc(4). In one embodiment, the carbohydrate moiety further consists essentially of a Gal(1) bound to GlcNAc(4). In another embodiment, the carbohydrate moiety further consists essentially of a Gal(1) bound to GlcNAc(4) and a Gal(2) bound to GlcNAc(3).

In one embodiment, fucosylated glycoprotein comprises a glycan moiety identical to the nonfucosylated glycan moiety described in the paragraph immediately preceding this paragraph, but also bears a fucose moiety at GlcNAc(1).

In one aspect, a genetically modified cell is provided, wherein the modification is to a FX gene, and wherein the modification results in the cell producing a FX mRNA that encodes an FX protein having at least one of the following amino acids: 79S, 90K, 136L, 211R, 289S; and wherein the cell exhibits a reduced ability to fucosylate a glycoprotein as compared with a cell that lacks the FX gene modification. In one embodiment, the mRNA encodes an FX protein comprising a serine at position 289. In another embodiment, the mRNA encodes an FX protein that further comprises at least one of a 79S, 90K, 136L, 211R.

In one aspect, a genetically modified cell is provided, wherein the modification is to a FX gene, wherein the modification alters a codon of the FX gene such that the modified FX gene codes for an FX protein having at least one of the following: a serine at position 79, a lysine at position 90, a leucine at position 136, an arginine at position 211, and a serine at position 289. In one embodiment the FX protein comprises a serine at position 289 and at least one of a lysine at position 90, a leucine at position 136, and/or an arginine at position 211.

In one embodiment, the cell further expresses an Fc-containing protein. In one embodiment, the Fc-containing protein is an antibody.

In one embodiment, the cell glycosylates the Fc-containing protein, but does not substantially fucosylate the glycosylated Fc-containing protein. In a specific embodiment, the fucosylation is about no more than 5%, 4%, 3%, 2%, 1%, or 0.5% of the fucosylation of the glycosylated Fc-containing protein as compared to a cell that lacks the FX gene modification.

In one embodiment, the glycosylation comprises a biantennary trimannosyl group. In one embodiment, the molar ratio of fucose to biantennary trimannosyl group is no more than about 1:20, 1:25, 1:33, 1:50, 1:100, or 1:200. In one embodiment, the molar ratio of fucose to biantennary trimannosyl group in the fucosylated Fc-containing protein is no more than about 1:20, 1:25, 1:33, 1:50, 1:100, or 1:200.

In one embodiment, the Fc-containing protein is an antibody, and the glycosylation comprises a glycan moiety at position 297 of the Fc. In one embodiment, the molar ratio of fucose to glycan moiety is no more than about 1:20, 1:20, 1:25, 1:33, 1:50, 1:100, or 200. In one embodiment, the glycan moiety comprises two tandem GlcNAc residues followed by a biantennary trimannosyl moiety, wherein each of two terminal mannosyl moieties of the trimannosyl moiety bear one GlcNAc residue. In one embodiment, the molar ratio of fucose to GlcNAc in the glycan is no more than 1:80, 1:100, 1:133, 1:150, 1:200, 1:400, or 1:800.

In one aspect, a modified mammalian cell that ectopically expresses a glycoprotein is provided, wherein the modification comprises a modified FX nucleic acid sequence, and the cell comprises a fucose salvage pathway and a de novo fucose synthesis pathway and expresses a functional FUT 8 protein and a functional GMD protein, wherein the de novo fucose synthesis pathway is incapable of substantially fucosylating a glycoprotein due to the modification of the FX nucleic acid sequence at about 37° C., but is capable of substantially fucosylating the glycoprotein at about 34° C.

The individual aspects and embodiments described herein are intended to be employed alone or in combination with any other aspect or embodiment, unless expressly stated otherwise or unless such combination is disallowed by the context.

BRIEF DESCRIPTION OF THE FIGURES

FIG. 1 shows a MacVector™ alignment for FX protein sequence (from top to bottom) of monkey (*Macacca mulatta*), SEQ ID NO:3; human, SEQ ID NO:4; mouse (*Mus musculus*), SEQ ID NO:5; rat (*Rattus norvegicus*), SEQ ID NO:6; CHO (*Cricetulus griseus*), SEQ ID NO:1; and CHO with an L289S and N90K modification (designated cell line 8088), SEQ ID NO:2.

FIG. 16 summarizes results of mass spectrometry studies on wild-type and low fucosylation cell lines. GlcNAc residues are represented by squares; mannose residues are represented by circles; galactose residues are represented by diamonds; fucose residues are represented by triangles.

DESCRIPTION

Figure 2:
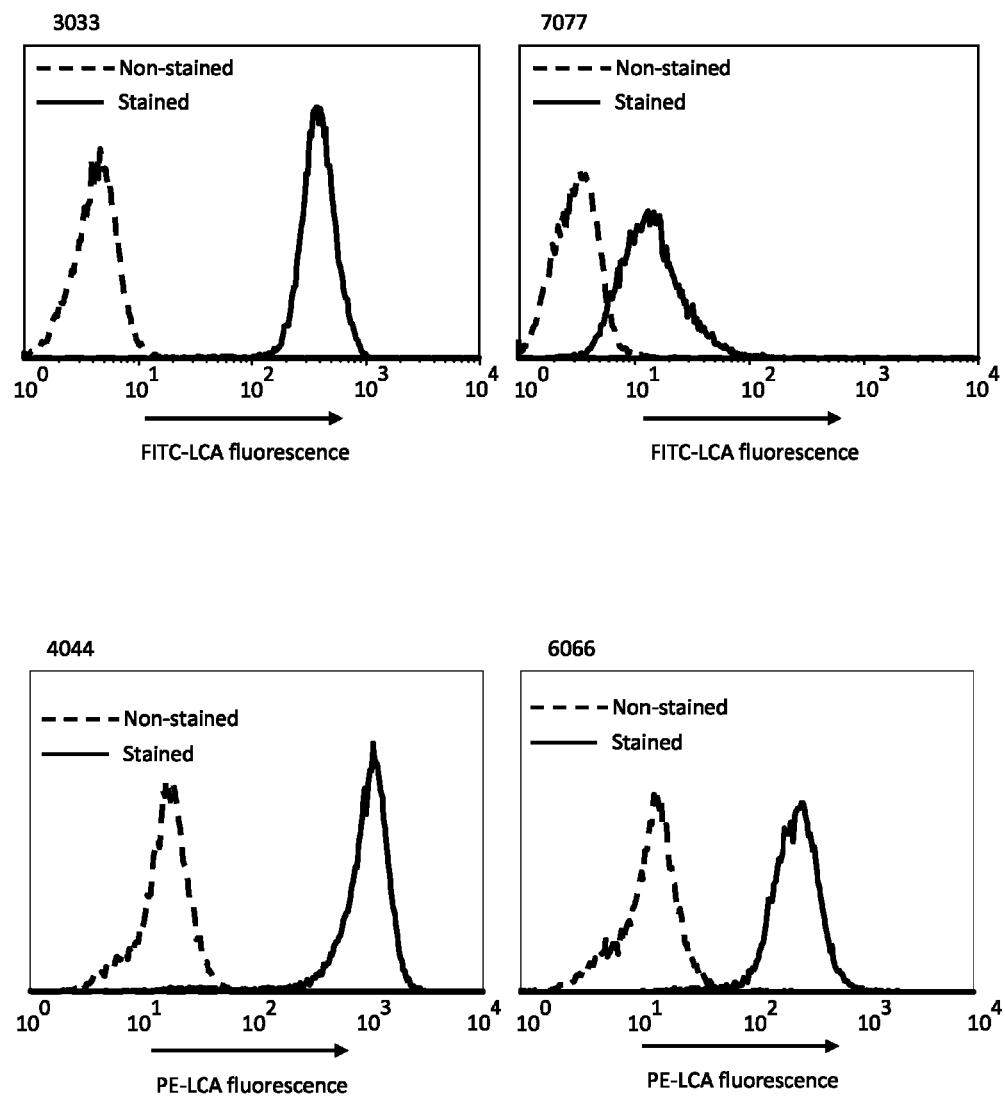
FIG. 2 shows flow cytometry histograms of 3033, 6066, 7077, and 8088 cells before and after staining with LCA.
Figure 3:
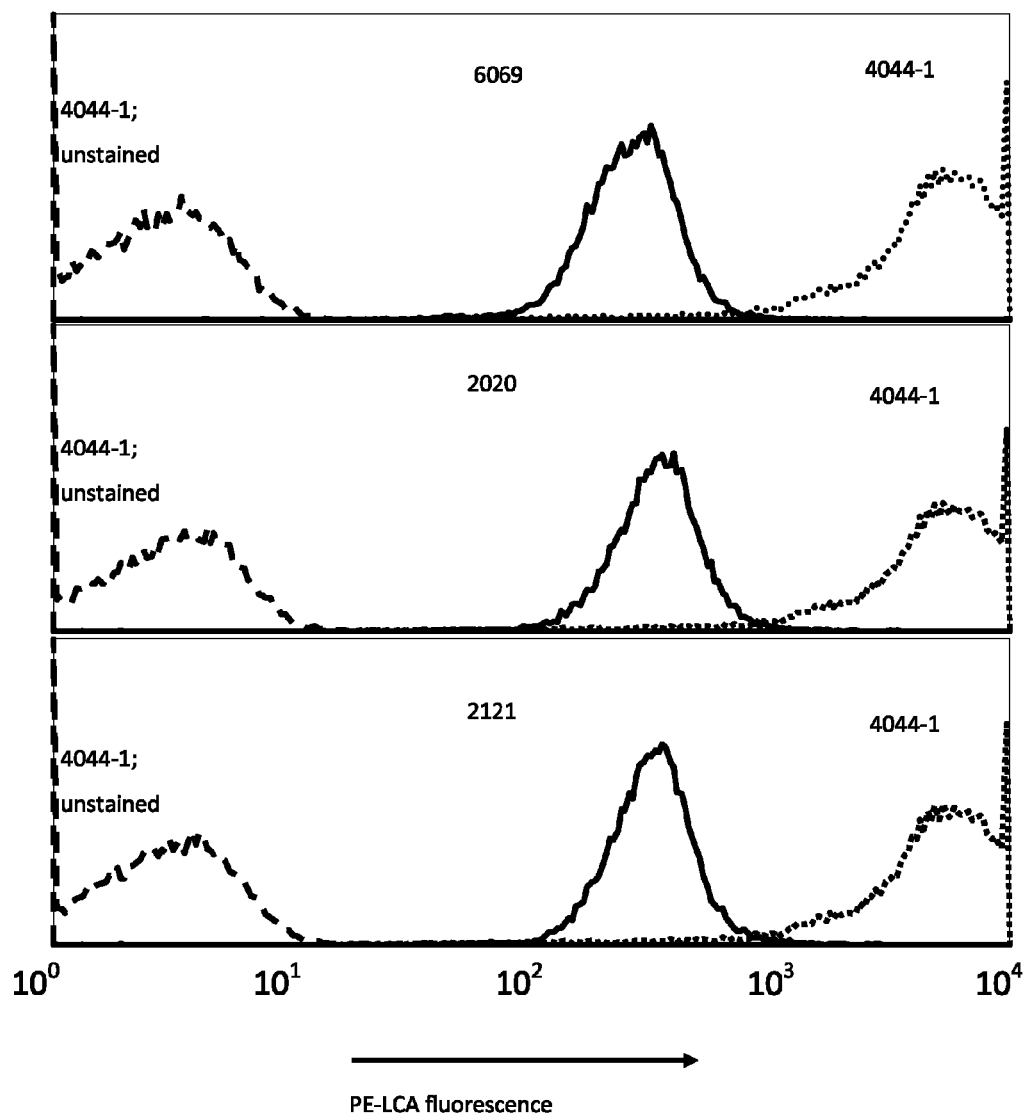
FIG. 3 shows flow cytometry histograms of unstained 4044-1 cells, and histograms of 4044-1, 6069, 2020, and 2121 cells stained with LCA.

The invention is not limited to particular methods and experimental conditions described, as such methods and conditions may vary. The terminology used herein is for the purpose of describing particular embodiments only, and is not intended to be limiting, since the invention is encompassed by the granted claims.

Unless defined otherwise, all terms and phrases used include the meanings that the terms and phrases have attained in the art, unless the contrary is clearly indicated or clearly apparent from the context in which the term or phrase is used. Although any methods and materials similar or equivalent to those described can be used in the practice or testing of the present invention, particular methods and materials are now described. All publications mentioned are hereby incorporated by reference.

Reference to the singular (e.g., "a" or "the") is intended to encompass reference to the plural, unless the context clearly indicates that reference to the plural is excluded.

The term "antibody" includes immunoglobulin molecules comprising four polypeptide chains, two heavy (H) chains and two light (L) chains inter-connected by disulfide bonds. Each heavy chain comprises a heavy chain variable (VH) region and a heavy chain constant region (CH). The heavy chain constant region comprises three domains, CH1, CH2 and CH3. Each light chain comprises a light chain variable (VL) region and a light chain constant region (CL). The VH and VL regions can be further subdivided into regions of hypervariability, termed complementarity determining regions (CDRs), interspersed with regions that are more conserved, termed framework regions (FRs). Each VH and VL comprises three CDRs and four FRs, arranged from amino-terminus to carboxy-terminus in the following order: FR1, CDR1, FR2, CDR2, FR3, CDR3, FR4 (heavy chain CDRs may be abbreviated as HCDR1, HCDR2 and HCDR3; light chain CDRs may be abbreviated as LCDR1, LCDR2 and LCDR3. The term "high affinity" antibody refers to an antibody that has a KD with respect to its target epitope about of $10^{-9}$ M or lower (e.g., about $1\times10^{-9}$ M, $1\times10^{-10}$ M, $1\times10^{-11}$ M, or about $1\times10^{-12}$ M). In one embodiment, KD is measured by surface plasmon resonance, e.g., BIACORE™; in another embodiment, KD is measured by ELISA.

The phrase "binding protein" includes any protein that is capable of specifically recognizing a binding partner. Specific recognition generally requires that the binding protein bind its binding partner with a dissociation constant (KD) of no higher than a few micromolar, and in most instances desirable binding proteins bind their binding partners in the nanomolar range, e.g., in various embodiments on the order of less than a hundred nanomolar. Most binding proteins described herein are also Fc-containing proteins, i.e., they comprise a binding moiety fused with an Fc that comprises at least a functional portion of an immunoglobulin CH2 and CH3 region. Typical binding proteins are antibodies, multispecific antibodies (e.g., bispecific antibodies), immunoadhesins, traps (e.g., cytokine traps such as IL-1 traps; VEGF trap, etc.). Typical binding proteins that are not antibodies bear a binding moiety (e.g., a receptor or fragment thereof, a ligand or fragment thereof, a variation on a canonical immunoglobulin variable domain, etc.) and an immunoglobulin moiety that frequently comprises a CH2 and a CH3 immunoglobulin domain (or fragment thereof retaining an Fc effector function). Thus, the compositions and methods of the invention can be used to make binding proteins (e.g., including immunoadhesins and traps) that bear an immunoglobulin region that binds an Fc receptor and/or that activates complement (e.g., a functional CH2 and CH3 region) and thereby is capable of mediating ADCC and/or CDC.

Multispecific antibodies may be specific for different epitopes of one target polypeptide or may contain antigen-binding domains specific for more than one target polypeptide. Multispecific binding proteins that are bispecific can be made that comprise two immunoglobulin arms, e.g., wherein the first arm of an immunoglobulin is specific for a first epitope, and the second arm of the immunoglobulin is specific for a second epitope. Other multispecific binding proteins include those wherein the second arm bears a binding moiety (a ligand or a receptor or binding fragment thereof) that specifically binds a target that is a protein or non-protein binding partner.

The phrase "bispecific antibody" includes an antibody capable of selectively binding two or more epitopes. Bispecific antibodies generally comprise two nonidentical heavy chains, with each heavy chain specifically binding a different epitope—either on two different molecules (e.g., different epitopes on two different antigens) or on the same molecule (e.g., different epitopes on the same antigen). If a bispecific antibody is capable of selectively binding two different epitopes (a first epitope and a second epitope), the affinity of the first heavy chain for the first epitope will generally be at least one to two or three or four or more orders of magnitude lower than the affinity of the first heavy chain for the second epitope, and vice versa. Epitopes specifically bound by the bispecific antibody can be on the same or a different target (e.g., on the same or a different protein). Bispecific antibodies can be made, for example, by combining heavy chains that recognize different epitopes of the same antigen. For example, nucleic acid sequences encoding heavy chain variable sequences that recognize different epitopes of the same antigen can be fused to nucleic acid sequences encoding the same or different heavy chain constant regions, and such sequences can be expressed in a cell that expresses an immunoglobulin light chain. A typical bispecific antibody has two heavy chains each having three heavy chain CDRs, followed by (N-terminal to C-terminal) a CH1 domain, a hinge, a CH2 domain, and a CH3 domain, and an immunoglobulin light chain that either does not confer epitope-binding specificity but that can associate with each heavy chain, or that can associate with each heavy chain and that can bind one or more of the epitopes bound by the heavy chain epitope-binding regions, or that can associate with each heavy chain and enable binding or one or both of the heavy chains to one or both epitopes.

One example of a bispecific binding protein format employs a first immunoglobulin (Ig) CH3 domain and a second Ig CH3 domain, wherein the first and second Ig CH3 domains differ from one another by at least one amino acid, and wherein at least one amino acid difference reduces binding of the bispecific antibody to Protein A as compared to a bispecific antibody lacking the amino acid difference. In one embodiment, the first Ig CH3 domain binds Protein A and the second Ig CH3 domain contains a mutation that reduces or abolishes Protein A binding such as a 435R modification (by EU numbering; 95R by IMGT exon numbering). The second CH3 may further comprise a 436F modification (by EU numbering; 96F by IMGT numbering). Further modifications that may be found within the second CH3 include 356E, 358M, 384S, 392N, 397M, and 422I (by EU numbering; 16E, 18M, 44S, 52N, 57M, and 82I by IMGT numbering). In this format, the first Ig CH3 domain is fused to a first binding moiety (e.g., a first Ig variable domain that specifically binds a first epitope), and the second Ig CH3 domain is fused to a second binding moiety (e.g., a second Ig variable domain that specifically binds a second epitope, wherein the first and the second epitopes are different).

The term "cell" includes any cell that is suitable for expressing a recombinant nucleic acid sequence. Cells include eukaryotes (single-cell or multiple-cell), yeast cells (e.g., *S. cerevisiae, S. pombe, P. pastoris, P. methanolica*, etc.), plant cells, insect cells (e.g., SF-9, SF-21, baculovirus-infected insect cells, *Trichoplusia ni*, etc.), non-human animal cells, human cells, or cell fusions such as, for example, hybridomas or quadromas. Cells that do not naturally comprise a pathway for fucosylation may be genetically modified to contain one (see, e.g., US Patent Application Publication No. 2010/0028951A1), and the cell can be modified to employ a FX gene that is modified as described herein.

In some embodiments, the cell is a human, monkey, ape, hamster, rat, or mouse cell. In some embodiments, the cell is eukaryotic and is selected from the following cells: CHO (e.g., CHO K1, DXB-11 CHO, Veggie-CHO), COS (e.g., COS-7), Syrian hamster, rat myeloma, mouse myeloma (e.g., SP2/0, NSO), retinal cell, Vero, CV1, kidney (e.g., HEK293, 293 EBNA, MSR 293, MDCK, HaK, BHK, BHK21), HeLa, HepG2, WI38, MRC 5, Colo205, HB 8065, HL-60, Jurkat, Daudi, A431 (epidermal), CV-1, U937, 3T3, L cell, C127 cell, MMT 060562, Sertoli cell, BRL 3A cell, HT1080 cell, a human myeloma cell, tumor cell, a human lymphoma cell (e.g., a Namalwa cell) and a cell line derived from an aforementioned cell. In some embodiments, the cell comprises one or more viral genes, e.g. the cell is a retinal cell that expresses a viral gene (e.g., a PER.C6™ cell).

The phrase "Fc-containing protein" includes antibodies, bispecific antibodies, immunoadhesins, and other binding proteins that comprise at least a functional portion of an immunoglobulin CH2 and CH3 region. A "functional portion" refers to a CH2 and CH3 region that can bind an Fc receptor (e.g., an FcγR or an FcRN), and/or that can participate in the activation of complement. If the CH2 and CH3 region contains deletions, substitutions, and/or insertions or other modifications that render it unable to bind any Fc receptor and also unable to activate complement, the CH2 and CH3 region is not functional.

Fc-containing proteins can comprise modifications in immunoglobulin domains, including where the modifications affect one or more effector function of the binding protein (e.g., modifications that affect FcγR binding, FcRN binding and thus half-life, and/or CDC activity). Such modifications include, but are not limited to, the following modifications and combinations thereof, with reference to EU numbering of an immunoglobulin constant region: 238, 239, 248, 249, 250, 252, 254, 255, 256, 258, 265, 267, 268, 269, 270, 272, 276, 278, 280, 283, 285, 286, 289, 290, 292, 293, 294, 295, 296, 297, 298, 301, 303, 305, 307, 308, 309, 311, 312, 315, 318, 320, 322, 324, 326, 327, 328, 329, 330, 331, 332, 333, 334, 335, 337, 338, 339, 340, 342, 344, 356, 358, 359, 360, 361, 362, 373, 375, 376, 378, 380, 382, 383, 384, 386, 388, 389, 398, 414, 416, 419, 428, 430, 433, 434, 435, 437, 438, and 439. For example, and not by way of limitation, the binding protein may exhibit enhanced serum half-life and have a modification at positions 252, 254, and 256; or a modification at 428 and/or 433 and/or 434; or a modification at 250 and/or 428; or a modification at 307 or 308, and 434.

Figure 1:
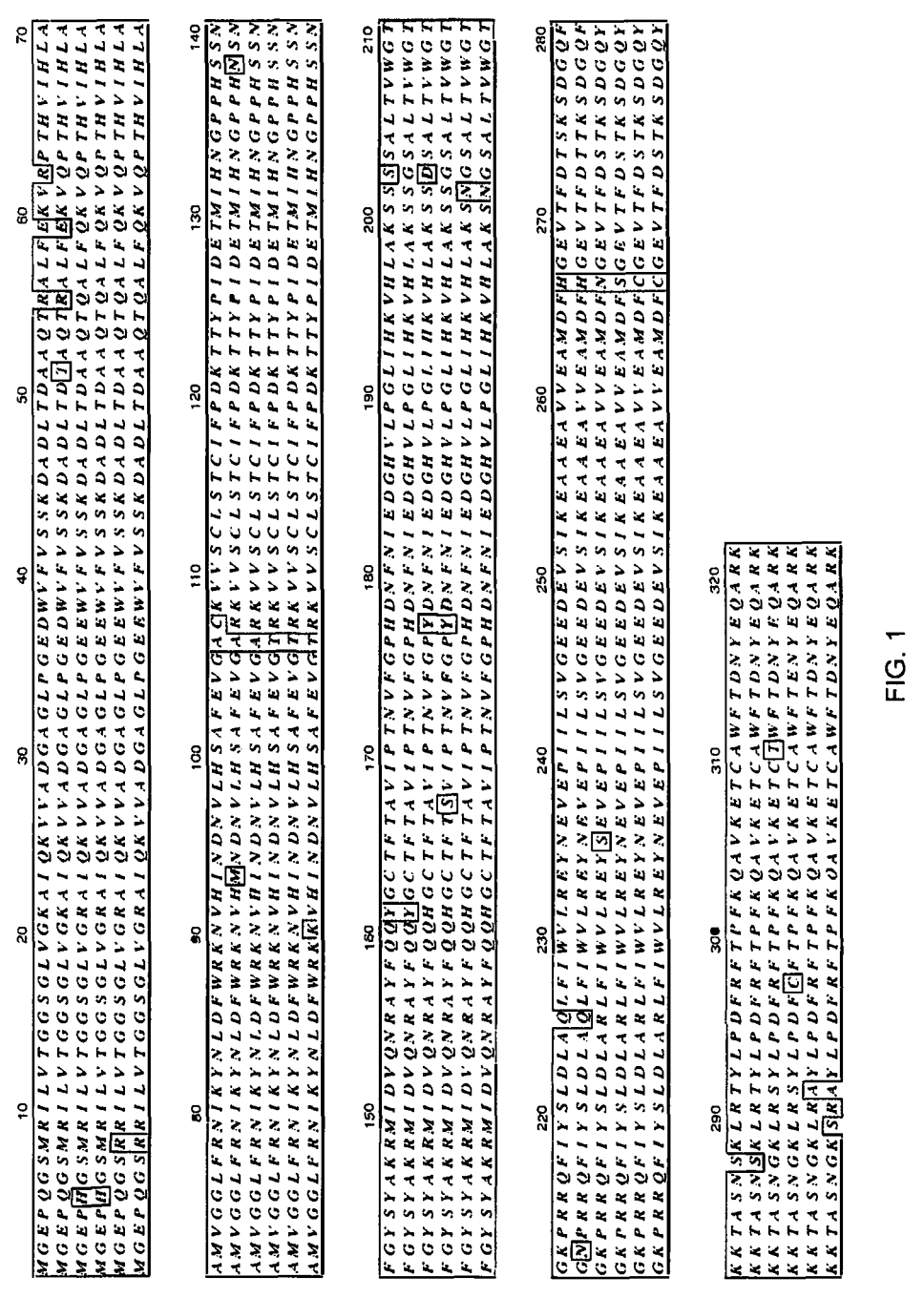

The term "FX" refers to a protein that exhibits GDP-4-keto-6-deoxymannose-3,5-epimerase-4-reductase activity or to a nucleic acid sequence that codes for a protein having GDP-4-keto-6-deoxymannose-3,5-epimerase-4-reductase activity. Most examples described herein refer to a wild-type *C. griseus* FX or a *C. griseus* FX that is modified according to the invention. However, "FX" is not limited to reference to a CHO cell. As shown in FIG. 1, an alignment of *Macaca mulatta*, human, *Mus musculus, Rattus norvegicus* FX sequences reveal a very high degree of conservation, i.e., FX sequences from various organisms are very, very similar. Based on this high degree of identity, it is to be expected that minor sequence differences that exist between these species will not substantially affect FX activity. Differences between the CHO FX sequence (SEQ ID NO:1) and sequences from monkey (SEQ ID NO:3), human (SEQ ID NO:4), mouse (SEQ ID NO:5), and rat (SEQ ID NO:6) include the following: 5H, 8M, 21K, 37D, 51T, 55R, 59E, 62R, 93M, 106A, 107C, 138N, 161Y, 167S, 177Y, 201S, 202S, 202D, 212N, 225Q, 235S, 266H, 266N, 266S, 273T, 274S, 280F, 287S, 291T, 291S, 297C, 310D, 314E. For the 321-amino acid wild-type CHO FX (SEQ ID NO:1), any one of monkey, human, mouse, and rat FX sequences can be recapitulated by selecting from 31 different substitutions, or 31/321×100=9.6% of the wild-type CHO FX sequence. Thus, a modified FX of the invention includes a wild-type CHO FX (e.g., SEQ ID NO:1) or an FX having at least a 90.4% identity with a wild-type CHO FX, and also bearing a substitution selected from the group consisting of N79S, N90K, G211R, and L289S. For less deviations from SEQ ID NO:1, a modified FX of the invention is at least 91%, 92%, 93%, 94%, 95%, 96%, 97%, 98%, or 99% identical with SEQ ID NO:1 and bears at least one modification selected from the group consisting of N79S, N90K, P136L, G211R, and L289S, e.g., bearing an L289S modification. A person of skill would expect that one or more of a small insertion or one or more of a small deletion that includes at least one of position 79, 90, 136, 211, and 289 would most likely also provide advantages associated with an embodiment of the invention (e.g., a cell bearing the modified gene would exhibit reduced fucosylation of a glycoprotein).

In a specific embodiment, the FX comprises a first substitution that is 289S and one or more of the second substitutions.

The phrase "low fucosylation" or "reduced fucosylation" refers to a lowered or reduced ability of a modified cell to fucosylate a glycoprotein as compared with a normal or wild-type cell. The glycoprotein may be an endogenous glycoprotein. More typically, the nucleic acid modification is made in a cell that is used to express a heterologous glycoprotein, e.g., a cell that expresses a binding protein (e.g., an antibody or bispecific antibody or an immunoadhesin or other Fc-containing glycoprotein) ectopically. For example, a CHO or PERC.6™ cell line modified according to the invention, which also expresses a human antibody, e.g., a human IgG1 antibody.

In general, reference to "low fucosylation" or "reduced fucosylation" with respect to a glycoprotein does not refer to a single glycoprotein molecule having less fucose residues attached to it. Rather, reference is made to a glycoprotein preparation prepared from cells, and the glycoprotein preparation comprises a population of individual glycoprotein molecules, with members of the population having different glycosylation features. For purposes of illustration and not limitation, for an IgG1 antibody expressed in a modified CHO cell according to the invention, "low fucosylation" or "reduced fucosylation" refers to a smaller number of individual glycoproteins having a fucose residue on an N-linked GlcNAc residue of a glycan at position 297 of the Fc. Such "low fucosylation" or "reduced fucosylation" can be characterized in a variety of ways (see elsewhere herein), but reference is in each case to a relatively low (or reduced) number of the glycoproteins of the population having fucose residues on them as compared to a population of the same glycoprotein made in a cell line that lacks a modification in accordance with the invention.

By way of illustration, if a glycoprotein made in accordance with the invention is 1% fucosylated as compared with the same glycoprotein made with a wild-type cell, only 1% of the molecules of Fc-containing protein are fucosylated in the inventive cell as compared with the amount of fucosylation observed in a corresponding wild-type cell (arbitrarily set to 100%, whether or not all of the molecules of Fc-containing protein are fucosylated in the wild-type cell under the same conditions).

In a "low fucosylation" or "reduced fucosylation" cell according to the invention, fucosylation of a glycoprotein is reduced about 90%, 91%, 92%, 93%, 94%, 95%, 96%, 97%, 98%, or 99% in comparison with a cell that does not contain the modification. In a specific embodiment, the reduction is about 99.1%, 99.2%, 99.3%, 99.4%, 99.5%, 99.6%, 99.7%, 99.8%, or 99.9% in comparison with a cell that does not contain the modification. In another specific embodiment, the reduction is about 98.1%, 98.2%, 98.3%, 98.4%, 98.5%, 98.6%, 98.7%, 98.8%, or 98.9% in comparison with a cell that does not contain the modification. In another specific embodiment, the reduction is about 97.1%, 97.2%, 97.3%, 97.4%, 97.5%, 97.6%, 97.7%, 97.8%, or 97.9% in comparison with a cell that does not contain the modification. In another specific embodiment, the reduction is about 96.1%, 96.2%, 96.3%, 96.4%, 96.5%, 96.6%, 96.7%, 96.8%, or 96.9% in comparison with a cell that does not contain the modification. In another specific embodiment, the reduction is about 95.1%, 95.2%, 95.3%, 95.4%, 95.5%, 95.6%, 95.7%, 95.8%, or 95.9% in comparison with a cell that does not contain the modification. In another specific embodiment, the reduction is about 94.1%, 94.2%, 94.3%, 94.4%, 94.5%, 94.6%, 94.7%, 94.8%, or 94.9% in comparison with a cell that does not contain the modification.

A glycoprotein preparation made in a cell according to the invention is fucosylated only about 5%, about 4%, about 3%, about 2%, about 1%, about 0.5%, about 0.4%, about 0.3%, about 0.2%, or about 0.1% of the amount of fucosylation of the same glycoprotein made in a cell that does not contain the modification.

Another way to characterize a glycoprotein preparation from a "low fucosylation" or "reduced fucosylation" cell is by the ratio of fucosylated to non-fucosylated glycoprotein in the glycoprotein preparation made by the cell. For example, a glycoprotein preparation made by a modified cell has a ratio of fucosylated glycoprotein:nonfucosylated glycoprotein that is about 1:10 through 1:15, 1:15 through 1:20, 1:20 through 1:40, 1:40 through 1:60, 1:60 through 1:80, 1:80 through 1:100, or 1:100 through 1:150.

Another way to characterize a glycoprotein preparation from a "low fucosylation" or "reduced fucosylation" cell is by the relative weight percent of nonfucosylated glycoprotein (as compared with total, i.e., fucosylated and nonfucosylated, glycoprotein). For example, a glycoprotein preparation made by a modified cell has a percent of nonfucosylated glycoprotein that is about 90%, about 95%, about 96%, about 97%, about 98%, about 99%, or about 99.5% as compared with the same glycoprotein preparation from a cell that lacks the modification.

Another way to characterize a glycoprotein preparation from a "low fucosylation" or "reduced fucosylation" cell is by the relative amount of fucose to glycan or relative amount of fucose to glycan component of the glycoprotein preparation. For example, in the case of Fc-containing proteins (e.g., antibodies), the glycosylation comprises a glycan at position 297, and the glycan comprises a biantennary trimannosyl moiety. In one embodiment, the molar ratio of fucose to glycan moiety is no more than about 1:20, 1:20, 1:25, 1:33, 1:50, 1:100, or 1:200. In one embodiment, the ratio of fucose to biantennary trimannosyl moiety is no more than about 1:20, 1:25, 1:33, 1:50, 1:100, or 1:200. In one embodiment, the molar ratio of fucose to biantennary trimannosyl moiety in the fucosylated Fc-containing protein is no more than about 1:20, 1:25, 1:33, 1:50, 1:100, or 1:200. In one embodiment, the glycan moiety comprises two tandem GlcNAc residues followed by a biantennary trimannosyl moiety, wherein each of two antennary terminal mannosyl moieties of the trimannosyl moiety bear one GlcNAc residue. In one embodiment, the molar ratio of fucose to GlcNAc in the glycan is no more than 1:80, 1:100, 1:133, 1:150, 1:200, 1:400, or 1:800.

In one embodiment, the amount of antibody protein made that is fucosylated is measured by overnight deglycosylation of antibody protein with PNGase F followed by oligosaccharide analysis via HPLC wherein fucosyl-containing oligosaccharides are quantified by integration of glycan peak area, and, e.g., protein fucosylation is calculated based on glycan peak area. The identity (and composition) of the glycan can be determined (and/or quantified) by any suitable method (e.g., mass spectroscopy).

The phrase "wild-type" includes reference to a cell or an activity that is not modified according to the invention, e.g., a cell that does not contain a modified FX nucleic acid sequence or modified FX protein. "Wild-type" FX activity includes reference to any parameter of activity (e.g., enzyme activity) that is exhibited by a natural or non-modified FX gene or protein. In comparing "wild-type" activity of an FX protein and activity of a modified FX protein, the "wild-type" FX protein and the modified FX protein are isolated in substantially the same manner from substantially the same source (e.g., same cell type, same organism) and compared under substantially the same conditions. In comparing "wild-type" FX activity and modified FX activity between wild-type cells and modified cells, FX activity is preferably measured under substantially the same or substantially similar conditions, with an identical or substantially identical glycoprotein.

Overview

Modified FX nucleic acid and protein sequences are provided, wherein modification results in a cell that is unable to support protein fucosylation in the absence of an external fucose source at a level that a cell bearing lacking the modification can support. The cells exhibit a substantially reduced ability to fucosylate glycoproteins (in the absence of a fucose source) at one temperature due to a disruption in an enzyme activity of the de novo pathway for synthesis of the substrate for glycoprotein fucosylation, GDP-L-fucose. At another (higher) temperature, the reduction in the cell's ability is minimal or unsubstantial.

The enzyme GDP-4-keto-deoxy-mannose-3,5,-epimerase-4-reductase (FX), participates in the de novo pathway of GDP-L-fucose synthesis, forming GDP-L-fucose from GDP-4-keto-6-deoxymannose. The resulting GDP-L-fucose can be used by a cell to make fucosylated proteins, including fucosylated antibodies. Since GDP-L-fucose synthetase participates in the de novo pathway, reduction in fucosylation in cells that lack sufficient FX activity can be rescued by a salvage pathway. The salvage pathway requires fucose, which is acted upon through the salvage pathway to form GDP-L-fucose, a substrate for protein fucosylation.

Certain modifications in FX result in the inability of a cell having a modified FX gene to sustain protein fucosylation in the absence of a fucose source, such that a cell bearing the modified enzyme and expressing, e.g., a recombinant antibody, exhibits a substantial reduction in the ability to fucosylate the antibody, as compared to a wild-type cell bearing wild-type FX gene.

The inability to sustain a sufficient rate or level of protein fucosylation due to the FX gene modifications described herein is substantially temperature-dependent. In particular, cells bearing a modified FX gene exhibit a substantial inability to sustain glycoprotein fucosylation at about 37° C. (e.g., 7% fucosylation of a human IgG1 isotype antibody), which is substantially relieved at about 34° C. (e.g., 70% fucosylation of the same antibody; see Table 3). Cells that have only a wild-type FX gene, in contrast, do not exhibit a large difference in the ability to sustain glycoprotein fucosylation at 37° C. as compared to 34° C.

De Novo and Salvage Pathways to GDP-Fucose

GDP-fucose is a central metabolite in the glycoprotein fucosylation pathway; it is the fucose donor in glycoprotein fucosylation. All known fucosyltransferases of interest that can fucosylate a glycoprotein comprising an Fc use GDP-fucose. Thus, for efficient glycoprotein fucosylation, a sufficient pool of GDP fucose must be generated and maintained at a sufficient level to match glycoprotein production.

There are two major pathways to GDP-fucose: a de novo synthesis pathway and a salvage pathway. In many mammalian cells, GDP-fucose can be made from an externally supplied carbon source (e.g., glucose) by a de novo fucosylation pathway. In the de novo pathway for fucosylation, glucose enters the cell through a transporter, and is converted to D-mannose-1-phosphate. D-mannose-1-phosphate is then converted by D-mannose-1-phosphate guanylyltransferase into GDP-mannose. GDP-mannose is converted to GDP-4-keto-6-deoxy-mannose by GDP mannose 4,6-dehydrates (GMD). GDP-4-keto-6-deoxy-mannose is converted to GDP fucose by GDP-4-keto-6-deoxy-mannose-3,5-epimerase-4-reductase (FX). GDP-fucose is a potent feedback inhibitor of GMD. GDP-fucose enters the Golgi apparatus through a GDP-fucose transporter. Once in the Golgi, the GDP-fucose is a substrate for α1,6-fucosyltransferase, which fucosylates glycoproteins.

In many mammalian cells, a salvage pathway for generating GDP-fucose from externally supplied fucose also exists. In the salvage pathway, fucose is transported into the cell and phosphorylated to form fucose-1-phosphate, which can be converted to GDP-fucose. The GDP-fucose is transported into the Golgi and is available as a substrate for the α1,6-fucosyltransferase. Fucose transport into the cell is presumably by facilitated diffusion and by lysosomal transport, and the salvage pathway appears to be universal in mammalian cells (see, e.g., Becker and Lowe (2003) Fucose: biosynthesis and biological function in mammals, *Glycobiology* 13(7):41R-53R).

Thus, in the absence of a fucose source, cells fucosylate glycoproteins using fucose generated by the de novo synthesis pathway. In the presence of fucose, cells fucosylate glycoproteins using fucose transported into the cell. Therefore, if the de novo synthesis pathway is blocked or damaged, glycoprotein fucosylation can still occur, but only in the presence of a fucose source.

The compositions and methods described enable cell lines that provide a conditional block in a pathway for fucosylating a glycoprotein by providing a genetically modified cell having a modification in an FX nucleic acid sequence. In cells that contain both a de novo and a salvage pathway, the cells provide enhanced versatility. In such cells in the absence of an external source of fucose, fucosylation of a glycoprotein can be substantially reduced at one temperature, but not substantially reduced at a second temperature. Alternatively, essentially wild-type rates or levels of glycoprotein fucosylation can be switched on by providing an external source of fucose, without regard to the temperature at which the cell is maintained.

FX Modifications

An isolated nucleic acid that encodes a modified FX protein sequence is provided. The isolated nucleic acid encodes an FX protein comprising an amino acid modification selected from the group consisting of 79S, 90K, 136L, 211R, 289S, and a combination thereof. In one embodiment, the isolated nucleic acid encodes an FX protein comprising a serine at position 289, in another embodiment comprising at least one of a 79S, 90K, 136L, and/or 211R.

The nucleic acid encoding the modified FX protein is used in any suitable form. Suitability of the form of the nucleic acid depends upon its use. For example, suitable forms include a cDNA that can be used in an expression vector for extrachromosomal expression in a cell, or which can be integrated (at a specific location, or randomly) into a genome of a cell. Suitable forms also include a genomic sequence, which is modified to encode the substitution(s) described herein. Suitable forms also include, for example, a targeting sequence (e.g., one or more targeting arms) for targeting the nucleic acid to a specific location in a genome, e.g., to replace one or both alleles of a native FX gene. Suitable forms include targeting vectors that target the nucleic acid to a specific location in a cell, e.g., to an FX locus, for replacement of an endogenous FX nucleic acid sequence with an FX nucleic acid sequence according to the invention. Modification of an endogenous FX sequence can be made at one or both alleles of the cell.

Cell Lines Faith Low or Reduced Fucosylation

Compositions and methods for low fucosylating cell lines are provided. The compositions include nucleic acids and proteins that, when present in a cell that lacks or substantially lacks a native or wild-type FX activity, confer upon the cell a reduced ability to fucosylate a glycoprotein, e.g., an Fc-containing glycoprotein such as, e.g., an antibody. In various embodiments, such cells include cells that exhibit a substantially reduced ability to fucosylate a glycoprotein at a first temperature (e.g., about 37° C.), but retain the ability to fucosylate the glycoprotein at a second temperature (e.g., about 34° C.). Thus, cells are provided that can be grown at a first temperature that is fucosylation-inhibiting, and growth conditions can be changed to a second temperature that is fucosylation-permissive.

Low fucosylating cell lines can be made using any suitable cells in conjunction with compositions and methods described herein. For example, and not by way of limitation, any cell lines commonly employed in the manufacture of biopharmaceuticals can be used. Certain methods and compositions for rendering such cell lines useful as low fucosylation cell lines are described herein; others are obvious or readily apparent by those skilled in the art in light of this description. Human cells (e.g., HeLa, PERC.6™, etc.), CHO cells, mouse cells, etc. can be genetically modified as described herein to generate a useful cell line. In the case of CHO cells, e.g., a useful low fucosylation cell line can be made by modifying a single allele of the FX gene due to the observation that CHO FX activity appears to be functionally haploid. In the case of other cells that exhibit a functional diploidy at the FX locus, on the other hand, can be manipulated by replacing one FX allele with a modified FX nucleic acid sequence as described herein and knocking out the second (wild-type) allele, or replacing both FX alleles with a modified FX nucleic acid sequence as described herein.

Resulting cells include those whose FX activity is wholly or substantially characterized as low fucosylating. That is, the cell need not be completely devoid of a wild-type FX protein or a wild-type FX gene; however, the cell—under an appropriate condition or set of conditions (e.g., a selected temperature)—should be unable or substantially unable to fucosylate a glycoprotein (e.g., an Fc-containing glycoprotein) at anywhere near the level that a corresponding cell with altogether normal FX activity can fucosylate the same glycoprotein.

Comparison of a cell according to the invention and a cell that does not contain the modification is conducted under the same or under essentially the same conditions (e.g., media, temperature, cell density, etc.). For example, in various embodiments the cell will exhibit an ability to fucosylate no more than 10% to no more than 1% of the ability to fucosylate that a wild-type cell exhibits. This comparison can be done, for example, by preparing a cell having the modification(s) described herein, and comparing the level of fucosylation of a glycoprotein expressed by the cell (e.g., expression of an antibody from an expression construct in the cell) to the level of fucosylation of the same glycoprotein expressed by a wild-type cell. For the comparison, the cells are grown at the same temperature and under the same conditions. Fucosylation level of the glycoprotein can be ascertained using any suitable analytical method known in the art for quantitating the amount of fucose present in a glycoprotein preparation.

In determining how much of the glycoprotein is fucosylated, the amount of fucose is compared with either the amount of total glycoprotein or with the amount of glycan obtained from the protein.

Fucosylation-Deficient Cell Lines

A number of mammalian cell lines that are altogether unable to fucosylate glycoproteins have been isolated. Development of fucosylation-deficient cell lines has been largely fueled by the need to make antibodies that lack fucosylation. Antibodies that lack fucosylation can mediate antibody-dependent cell-mediated cytotoxicity (ADCC) far better than fucosylated antibodies, due to altered binding to an Fc receptor. Antibodies that mediate ADCC better are therefore highly desirable, particularly antibodies that comprise variable regions that target tumor cells. Cells that are unable to fucosylate glycoproteins are thus widely used in the development and manufacture of antibodies for therapeutic uses.

Two fucosylation pathway knockouts have been developed that result in a cell's inability to fucosylate a glycoprotein. Knockout of α1,6-fucosyltransferase (FUT8) results in the inability to transfer GDP-fucose to a glycoprotein. Knockout of GDP mannose 4,6-dehydratase (GMD) results in the inability to make GDP-4-keto-6-deoxy-mannose from GDP-mannose in the de novo pathway.

Fucosylation knockouts downstream of GDP-fucose formation, e.g., α1,6-fucosyltransferase knockouts, cannot resort to the salvage pathway to fucosylate glycoproteins in the presence of an external fucose source. This is because the block is distal to the formation of GDP-fucose, the metabolite at which the de novo and salvage pathways meet. Therefore, feeding cells that have such a knockout with fucose will not rescue glycoprotein fucosylation. Thus, α1,6-fucosyltransferase knockouts offer no simple route to selectively manipulating a cell's ability to fucosylate a glycoprotein.

Fucosylation knockouts upstream of GDP-fucose formation, e.g., GMD knockouts, can theoretically resort to the salvage pathway to fucosylate glycoproteins. This is because the block occurs before formation of GDP-fucose. Feeding such cells with fucose will theoretically rescue glycoprotein fucosylation. Cell lines that contain knockouts, however, lack versatility.

The inventors have found that a selective disruption of the de novo fucosylation pathway prior to formation of GDP-fucose will generate a cell line with a defect that is rescued by providing a source of fucose, or rescued by maintaining the cells under conditions that are permissive for fucosylation. The inventors have modified cells to have a defect in the de novo pathway upstream of GDP-fucose and that can be grown in the absence of fucose under a first condition and exhibit a substantially reduced ability to fucosylate a glycoprotein, whereas under a second condition the cells can effectively fucosylate a glycoprotein even in the absence of an external fucose source. Such a particularly versatile cell line presents the option of turning fucosylation on or off in the cell line by controlling the availability of an external source of fucose (or a suitable fucose precursor) and/or growing cells under a fucosylation-permissive condition or a fucosylation-deficient condition.

The inventors have selectively disrupted the de novo pathway for GDP-fucose synthesis by generating a mutated FX nucleic acid sequence. The FX protein is a bifunctional epimerase-reductase that epimerizes the C3 hydroxyl and the C5 methyl groups of mannose, forming GDP-4-keto-6-deoxygalactose. An NADPH-dependent reductase activity of the bifunctional enzyme then reduces the keto moiety to form GDP-fucose. The FX gene is highly conserved, which is reflected in the high degrees of identity and similarity in FX proteins. See, e.g., Becker and Lowe (2003) Fucose: biosynthesis and biological function in mammals, Glycobiology, 13(7):41R-53R. Thus, the data presented in connection with FX mutations in CHO cells is applicable to corresponding FX modifications in a wide variety of cells.

The selective FX disruption provides an enhanced versatility, which allows a practitioner to disfavor, or inhibit, fucosylation by maintaining a culture at a first temperature; but allow fucosylation by maintaining the culture at a second temperature. In various embodiments this illustrated by a modified FX gene, wherein the modification comprises a modification selected from the group consisting of (for a CHO FX protein) L289S, N79S, N90K, P136L, G211R, and a combination thereof. In various embodiments, the FX modification consists essentially of a modification selected from the group consisting of L289S, L289S/N90K, L289S/G211R, L289S/P136L, L289S/N79S, and a combination thereof.

As those skilled in the art know, certain cells that are diploid display phenotypes that reflect activity of only one of two alleles at particular loci, e.g., CHO cells, and with respect to those loci appear to be functionally haploid (or hypodiploid) from a phenotypic perspective. In such cells, modification of even a single allele as described herein may result in a phenotype that essentially reflects the activity of the modified allele, even in cases where the phenotype is not a dominant phenotype. For example, in CHO cells, modification as described herein of a single allele will likely result in a FX phenotype essentially as described herein, presumably due to nonexpression (or hypoexpression) of the wild-type FX allele.

In various embodiments, the FX is an FX that is not from a CHO cell, and the modification comprises a modification selected from the group consisting of a modification that corresponds in the non-CHO FX to the CHO modifications listed above. Corresponding modifications can be identified by aligning the CHO FX protein sequence with any other FX sequence of interest (with or without gaps in the alignment) using, e.g., a general purpose multiple sequence alignment algorithm such as ClustalW with default parameters (e.g., for human (Accession No. AAC50786) and *C. griseus* (Accession No. AAM91926) FX, using MacVector™ v. 10.0.2, pairwise: Gonnet matrix at slow alignment speed, open gap penalty=10.0, extend gap penalty=0.1; multiple: Gonnet series, open gap penalty=10.0, extend gap penalty=0.2, delay divergent=30%, gap separation distance=4, no end gap separation, residue-specific penalties, and hydrophilic penalties (hydrophilic residues GPSNDQEKR)).

As a practical matter, aligning a subject sequence against SEQ ID NO:1 or SEQ ID NO:1 and 3-6 in MacVector™ using the pairwise alignment default parameters will identify corresponding positions in the subject sequence at which to make modifications at positions equivalent to the CHO N79, N90, P136, G211, and L289, positions.

Glycoproteins

The compositions and methods can be used to modify the fucosylating ability of cells to achieve low fucosylation of any glycoprotein of interest. Although the majority of this disclosure refers to advantages of reduced fucosylation in antibodies, the benefits of the invention are not limited to antibodies. Any binding protein that bears an Fc—and there are many, many types of such binding proteins—can be made using the compositions and methods of the invention.

A typical glycoprotein that can be made with the invention is an antibody (e.g., a human, mouse, or humanized antibody) that is glycosylated and, under normal conditions in a wild-type cell, fucosylated. Examples include, by way of illustration and not by way of limitation, human antibodies of the IgG1, IgG2, and IgG4 subtypes. Glycoforms of such antibodies include those with a glycan moiety at position 297. Typical glycoforms at position 297 include an N-linked GlcNAc, followed by a GlcNAc, followed by a biantennary trimannosyl moiety, followed by (on each of two mannosyl moieties of the biantennary trimannosyl moiety) one or more GlcNAc residues, optionally followed by a galactose residue on one or more of the GlcNAc residues attached to the antennae of the biantennary trimannosyl moiety. Fucosylation of the glycan normally occurs at the N-linked initial GlcNAc residue, where (normally) a single fucose residue is linked via a fucosyltransferase to the 297-glycolated antibody. In various embodiments, the molar ratio or percent or extent of fucosylation of the antibody is measured with respect to this fucose residue in relation to the amount (or moles) of antibody and/or the amount (or moles) of glycan or glycan substituent (e.g., relative moles of fucose:antibody, or to fucose:GlcNAc or fucose:mannose or fucose:trimannosyl moiety or fucose:galactose of the 297-linked glycan, in an antibody preparation obtained from wild-type cells or from cells comprising a modified FX nucleic acid sequence in accordance with the invention).

Low-Fucosylation CHO Lines

A low fucosylation CHO line was constructed from CHO K1 cells adapted to grow in suspension in a serum-free bioreactor medium. The CHO line (designated line 6066) contained an L289S substitution in the CHO FX gene. A recombinant antibody that is a human IgG1 that specifically binds an interleukin receptor (Antibody 1) and a recombinant antibody that is a human IgG1 that specifically binds a cell surface protein of an immune cell (Antibody 2) were made in the cell line, and in a corresponding CHO cell line that lacks the FX modification (designated line 4044) as described in the examples. Cells were grown for three days in shakers or 12 days in a bioreactor (each at 37° C.).

Cells that bore the FX gene modification and expressed Antibody 1 fucosylated only about 6.14 or 6.86% (12 days) or about 7 or 8% (three days) of Antibody 1, whereas in the absence of the FX modification cells fucosylated about 89.3% (3 days) or about 85.8% (12 days) (Table 1).

Cells that bore the FX gene modification and expressed Antibody 2 fucosylated Antibody 2 only about 3.6%, whereas in the absence of the FX gene modification cells fucosylated about 95% (3 days) or about 76.8% (12 days) (Table 1).

Another low fucosylation CHO line was made from CHO K1 cells that contained an L289S and a N90K modification of the CHO FX gene (designated line 8088). Antibody 1 expressed in these cells exhibited only about 0.96% fucosylation (3 days) or 0.71% fucosylation (12 days) (Table 2).

Another low fucosylation CHO line was made from CHO K1 cells (from 6066-1 cells, which have an L289S FX gene modification) that contained a P136L substitution (designated line 2121). These cells expressed Antibody 1 that was only 0.82% fucosylated at 3 days (Table 2).

Two further low fucosylation CHO lines were made from CHO K1 cells (from 6066-1 cells, which have an L289S FX gene modification) that contained a N79S substitution (designated lines 2020 and 6069). These cells expressed Antibody 1 that was only 0.94% fucosylated at 3 days (2020) or only 0.86% fucosylated at 3 days (6069) (Table 2).

Temperature dependence of fucosylation for Antibody 1 was tested using cell lines 4044-1 (no FX gene modification) and cell line 6066-1 (L289S FX gene modification). Cell line 6066-1 exhibited only 7% fucosylation at 37° C., and about 70% fucosylation at 34° C. Cell line 4044-1 exhibited about the same fucosylation (95-96%) at both 37° C. and 34° C.

Two further low fucosylation cell lines were made from cell line 8088 (L289S and N90K) that expressed two different antibodies to the same growth factor receptor, Ab 3.1 and Ab 3.2. After growing for three days at 37° C. in the presence (salvage pathway) or absence (de novo pathway) of fucose, glycan composition and fucose content of the glycan was determined. In the absence of fucose, the cell lines produced only about 1.87% or 5.73% fucosylation, whereas in the presence of an external fucose source fucosylation was restored to at least 95.22% or 95.63%.

EXAMPLES

Example 1: CHO Cell Lines

A variety of CHO cell lines, isolated directly or indirectly from CHO K1 cells, are described herein.

RGC10 Cells.

The CHO cell line 3033 was generated from CHO K1 cells as described for RGC10 cells in U.S. Pat. No. 7,435, 553, hereby incorporated by reference. Briefly, CHO K1 cells were stably transfected with vector pTE158 and pcDNA6/TR (Invitrogen). Transfected cells were screened for doxycycline-inducible expression of hFcγR1, and one clone was selected to give rise to the 3033 cell line. 3033 cells were adapted to grow in suspension culture in serum-free Medium 3.

5055 Cells.

5055 cells are CHO K1 cells that have been adapted to grow in suspension in serum-free bioreactor medium Medium 2.

4044 Cells.

4044 cells were derived from RGC16 cells described in International Patent Application Publication No. WO 2008/151219 A1 filed 4 Jun. 2008, and US Patent Application Publication No. 2009/0124005A1 filed 4 Jun. 2008, each hereby incorporated by reference, and which contains a loxed cassette at an enhanced expression and stability (EESYR) locus. The EESYR locus in 4044 has, from 5' to 3' on the coding strand, a loxP site, an SV40 late promoter, a puromycin-resistance gene, a CMV promoter, an IRES, an eCFP gene, a lox2272 site, a CMV promoter, a DsRed gene, and a lox511 site. 4044 cells further contain a stably transfected pcDNA6/TR vector.

Other Cells.

The 7077 cell line was derived from 3033 cells without the use of exogenous recombinant nucleic acid. 6066, 8088, and 1010 cell lines were derived from 4044 cells without the use of exogenous recombinant nucleic acid.

Example 2: Production of Recombinant Antibodies in CHO Cells

Vectors. The vectors described herein have the features indicated, where the relative placement of the features is presented with respect to the coding strand, listed 5' to 3'.

pR4000: a human UbC promoter, a gene encoding the heavy chain of Ab 2, an SV40 late promoter, and a hygromycin resistance gene.

pR4001: a human UbC promoter, a gene encoding the light chain of Ab 2, an SV40 late promoter, and a puromycin resistance gene.

pR4002: a LoxP site, a human CMV promoter, a gene encoding the heavy chain of Ab 2, an SV40 late promoter, and a Lox2272 site.

pR4003: a Lox2272 site, a hygromycin-resistance gene, an IRES, an EGFP gene, a human CMV promoter, a gene encoding the light chain of Ab 2, and a Lox511 site.

pR4004: an SV40 late promoter and the gene encoding Cre recombinase (see WO 2008/151219A1, hereby incorporated by reference).

pR4005: a LoxP site, a human CMV promoter, a gene encoding the light chain of Antibody 1 (Ab 1), a SV40 late promoter, and a Lox2272 site.

pR4006: a Lox2272 site, a hygromycin resistance gene, an IRES, an EGFP gene, a human CMV promoter, a gene encoding the heavy chain of Ab 1, and a Lox511 site.

pR4007: a LoxP site, a human CMV promoter, a gene encoding the light chain of Ab 1, a SV40 late promoter, a gene encoding the N terminus of the hygromycin resistance protein, and a Lox2272 site.

pR4008: a Lox2272 site, a gene encoding the C terminus of hygromycin resistance protein, an IRES, an EGFP gene, a human CMV promoter, a gene encoding the heavy chain of Ab 1, and a Lox511 site.

pR4009: a LoxP site, a SV40 late promoter, a hygromycin resistance gene, an internal ribosome entry site (IRES), an EGFP gene, a human CMV promoter, and a Lox511 site.

pR4010: a LoxP site, an SV40 late promoter, a hygromycin resistance gene, an IRES, an EGFP gene, a human CMV promoter, the wild type FX gene, and a Lox511 site.

pR4010: a LoxP site, an SV40 late promoter, a hygromycin resistance gene, an IRES, an EGFP gene, a human CMV promoter, and the mutated FX gene having mutations L289S and N90K.

Fucosylation proficiency in CHO cells was studied by cell surface LCA staining and by analysis of recombinant antibodies produced from CHO cells. In one study, 7077 cells were used as the host cells for the expression of Antibody 2 (Ab 2), a human IgG1 antibody against a human B cell receptor, following a method described in U.S. Pat. No. 7,435,553, hereby incorporated by reference. Briefly, $1 \times 10^7$ 7077 cells were transfected with plasmid pR4000 (heavy chain, hygromycin resistance) and pR4001 (light chain, puromycin resistance) using Lipofectamine™ (Invitrogen, Carlsbad, Calif.). The transfected cultures were selected with 400 micrograms/mL hygromycin and 10 micrograms/mL puromycin each for two weeks in F12 medium containing 10% fetal calf serum. Cells that survived selection were pooled together and were adapted to grown in suspension in serum-free bioreactor medium Medium 2. Expression of hFcγRI was induced by the addition of doxycycline to the culture medium for three days. The induced cultures were incubated with 1 milligram/mL rabbit IgG for 18 hours prior to staining with F(ab')$_2$ fragment of a goat polyclonal FITC-conjugated anti-human Fc antibody (Jackson ImmunoResearch, West Grove, Pa.). The cells were stained for 1 hour then washed twice with PBS prior to analysis by flow cytometry on a MoFlo™ cell sorter (Fort Collins, Colo.). Cells with mean FITC fluorescence intensity in the top 5% of the total cell population were sorted into a pool and was named 7077-1 cells. 7077-1 cells were expanded for 10 days in Medium 2. To produce recombinant Ab 2, 7077-1 cells were seeded at $4 \times 10^5$ cells/mL Medium 2 in a shaker flask at 37° C. Three days later, the conditioned medium was collected and the Ab 2 protein wherein was purified by Protein A affinity chromatography.

4044 and 6066 CHO cells were used as host cells for the expression of Ab 2 and Ab 1, a human IgG1 antibody against a human cytokine receptor. Briefly, to express Ab 2, $2 \times 10^6$ 4044 and $2 \times 10^6$ 6066 cells (each having a loxed cassette at an EESYR locus) were each transfected with pR4002 (heavy chain in a loxed cassette), pR4003 (light chain and hygromycin resistance in a loxed cassette), and pR4004 (encodes Cre). To express Ab 1, $2 \times 10^6$ 4044 and $2 \times 10^6$ 6066 cells were each transfected with pR4005 (light chain in a loxed cassette), pR4006 (heavy chain and hygromycin resistance in a loxed cassette), and pR4004 (encodes Cre). Transfected 4044 and 6066 cells were selected with 400 micrograms/mL hygromycin for 10 days in F12 medium containing 10% FCS. Surviving cells were adapted to grow in suspension in serum-free Medium 1 for seven days. Cells that have undergone Cre-mediated cassette exchange at the EESYR locus expressed EGFP but not DsRed or ECFP. Cells positive for EGFP but negative for DsRed and ECFP were collected by cell sorting using a MoFlo™ sorter. The 4044-derived cells that were transfected with Ab 2 and Ab 1 genes were designated 4044-2 and 4044-1 cells, respectively. The 6066-derived cells that were transfected with Ab 2 and Ab 1 genes were designated 6066-2 and 6066-1 cells, respectively. 4044-2, 6066-2, 4044-1, and 6066-1 cells were expanded by culturing in Medium 2 for seven days. To produce recombinant antibodies, the four cell lines were seeded at $4 \times 10^5$ cells/mL medium 2 in a shaker flask at 37° C. Three days later, the conditioned media were collected and the recombinant antibodies therein were purified by Protein A affinity chromatography.

8088 and 1010 CHO cells were also used as host cells for the expression of Ab 1. Briefly, to express Ab 1, $2 \times 10^6$ 8088 and $2 \times 10^6$ 1010 cells were each transfected with pR4007 (light chain and first portion of hygromycin resistance gene in a loxed cassette), pR4008 (heavy chain and second portion of hygromycin resistance gene in a loxed cassette), and pR4004 (encoding Cre). Transfected cells that survived selection with 400 micrograms/mL hygromycin were adapted to grow in suspension in serum-free Medium 1. Cells that expressed EGFP but not DsRed or ECFP from the transfected 8088 and 1010 were isolated by cell sorting on a MoFlo™ and were designated 8088-1 and 1010-1. To produce Ab 1 protein, 8088-1 and 1010-1 cells were seeded in shaker flasks at $4\times10^5$ cells/mL. Three days later, the culture media were collected and the Ab 1 therein were purified by Protein A chromatography.

Example 3: Antibody Fucosylation Analysis

Purified human IgG1 antibody proteins were initially deglycosylated with PNGase F under denatured condition (0.5% SDS, 2 mM TCEP, and blocked with 1% NP-40) in 50 mM Tris pH 8.0 with protein/enzyme ratio of 1 microgram/ 0.1 mU at 37° C. overnight. The released glycans were then fluorescently derivatized with anthranilic acid at 80° C. for 1 hour. The samples were pre-cleaned to remove excess anthranilic acid reagent with Waters Oasis™ HLB cartridges. The oligosaccharide mixture was then analyzed by reversed phase HPLC, using 0.5% TFA in ddH$_2$O as mobile phase A, and 0.045% TFA in 90% acetonitrile/10% ddH$_2$O as mobile phase B. The glycans were resolved on a Thermo Hypercarb™ (Thermo Fisher, Waltham, Mass.) column (dimension of 100×2.1, particle size of 3 micrometers) through applying a gradient from 30 to 40% B over 40 minutes. The signals were detected using a fluorescence detector with an excitation wavelength of 230 nm, and emission wavelength of 425 nm. Further analysis of the HPLC-separated glycan peaks through mass spectrometry revealed that they were separated into two main groups; non-fucosylated bi-antennary glycans and fucosylated bi-antennary glycans. Within each group (fucosylated vs. non-fucosylated), the glycans were further separated into digalactosyl (G2), monogalactosyl (G1) or agalactosyl (G0) forms. Integration of the peak area corresponding to different glycan forms allow for the quantification on the populations of each individual glycans on the monoclonal antibody.

Example 4: Sequencing Major Transcripts of FX, GMD, GDP-fucose Transporter, and FUT8 Genes Proteins encoded by the FX, GMD, GDP-fucose transporter, and FUT8 genes are components the de novo fucosylation pathway. Sequences of the major transcript of FX gene in CHO cell lines 5055, 4044-1, 7077-1, 6066-1, 2121, 2020, 6069, 1010, and 8088 cells, and sequences of the major transcript of the GMD gene in 4044-1, 6066-1, 1010, and 8088 cells were determined. Sequences of the major transcripts expressed from the FUT8 and GDP-fucose transporter gene were also determined in 4044-1 and 6066-1 cells.

Briefly, total RNA was isolated from $5\times10^6$ CHO cells using Micro-Fast Track 2.0 Kit™ (Invitrogen, Carlsbad, Calif.). cDNAs for the four fucosylation genes were synthesized from total RNA using Oligo-dT as the primer and SuperScript III First-Strand Synthesis System™ (Invitrogen). GMD cDNA was PCR amplified using primers 5'-ctacaatctt ggtgcccaga gc-3' SEQ ID NO:7 and 5'-tccagttcag tttctgctgc g-3' SEQ ID NO:8. FX cDNA was PCR amplified using primers 5'-ttccctgaca agaccaccta tcc-3' SEQ ID NO:9 and 5'-tagttgtcgg tgaaccaggc ac-3' SEQ ID NO:10. GDP-fucose transporter cDNA was PCR amplified using primers 5'-gatgaggaca gcaggaacaa gc-3' SEQ ID NO:11 and 5'-agcactcttc tcaccctctt tgg-3' SEQ ID NO:12. FUT8 cDNA was PCR amplified using primers 5'-agccaagggt aagtaaggag gacg-3' SEQ ID NO:13 and 5'-ttgtagacag cctccatcct cg-3' SEQ ID NO:14. The DNA polymerases used in the PCR reactions were a 20 to 1 mix of Platinum Taq™ (Invitrogen) and cloned Pfu (Stratagene, La Jolla, Calif.). FOR products were purified after gel electrophoresis and cloned into pCR2.1 TOPO™ vector (Invitrogen) following the manufacturer's instructions. Cloned DNA products were transformed into electro-competent DH10B cells. A minimum of three bacterial colonies from each transformation were picked to inoculate three liquid cultures containing LB and 100 micrograms/mL ampicillin. Plasmid DNAs in these cultures were purified using QIAprep Spin Miniprep Kit™ (Qiagen). Sequences of the cloned PCR products were determined using the M13 primers located on the vector and the respective 5' and 3' FOR primers. These sequences were compared to Genbank sequences for FX (accession number AF525365), GMD (accession number AF525364), GDP-fucose transporter (accession number AB222037), and FUT8 (accession number BD359138) mRNA from *C. griseus*.

Mutations in consensus FX transcript sequences resulting in codon changes from the Genbank reference sequence (AF525365) were identified in 7077-1, 6066-1, 2121, 2020, 6069, 1010, and 8088 cells (Table 1 and 2). Sequences of the GMD transcripts from 4044-1, 6066-1, 1010, and 8088 cells matched GMD sequences reported in GenBank (accession number AF525364). Sequences of the GDP-fucose transporter and FUT8 transcripts in 4044-1 and 6066-1 cells matched their respective sequences reported in GenBank as well (accession numbers AB222037 and BD359138).

Example 5: Fucosylation in CHO Cell Lines with a Single L289S Mutation in the FX Gene Relative fucosylation proficiency in 3033, 4044, 6066, and 7077 cells were first studied by staining the cells with the lectin *Lens culinaris* agglutinin (LCA). Briefly, $2\times10^6$ 4044 and 6066 cells were each incubated with biotin-LCA (Vector Laboratories, Burlingame, Calif.) at 5 micrograms/ mL for one hour. After two washes with PBS, the cells were incubated with phycoerythrin-conjugated streptavidin (Jackson ImmunoResearch) for 30 minutes. The cells were then washed once with PBS and analyzed by flow cytometry. 3033 cells and 7077 cells were stained with FITC-LCA for one hour, washed twice, and analyzed by flow cytometry (FIG. 2). 3033, 4044, 6066, and 7077 cells were all stained by LCA. LCA staining intensity on 6066 and 7077 cells were significantly weaker than the LCA staining intensity on 3033 and 4044 cells (FIG. 2), suggesting that there was less protein fucosylation in 6066 and 7077 cells than in 3033 and 4044 cells. To examine whether 6066 and 7077 cells could be used as host cells for the expression of hIgG1 antibodies with low fucose content, 4044 and 6066 cells were stably transfected with expression plasmids for Ab 2 and Ab 1, and 7077 cells were stably transfected with expression plasmids for Ab 2 (see Example 2). Recombinant Ab 2 and Ab 1 were produced from the transfected cells in three-day shaker flask cultures as well as in twelve-day fed-batch bioreactor cultures. Ab 2 and Ab 1 were purified from the conditioned media and the levels of their fucosylation were determined by HPLC (Table 1). As shown in Table 1, 7077-1, 6066-1, and 6066-2 produced recombinant antibody with fucosylation level between 3.6% and 8% in shakers and bioreactors at 37° C.

TABLE 1

| Host Cell Line Designation | Production Cell Line Designation | Consensus FX Mutation | Reporter Antibody | Fucosylation in shaker (%) | Fucosylation in bioreactor (%) |
|---|---|---|---|---|---|
| 4044 | 4044-1 | None | Ab 1 | 89.3 | 85.8 |
| 7077 | 7077-1 | L289S | Ab 2 | 4.0 | |
| 4044 | 4044-2 | None | Ab 2 | 95 | 76.8 |
| 6066 | 6066-1 | L289S | Ab 1 | 7; 8 | 6.14; 6.86 |
| 6066 | 6066-2 | L289S | Ab 2 | 3.6 | |

Figure 4:
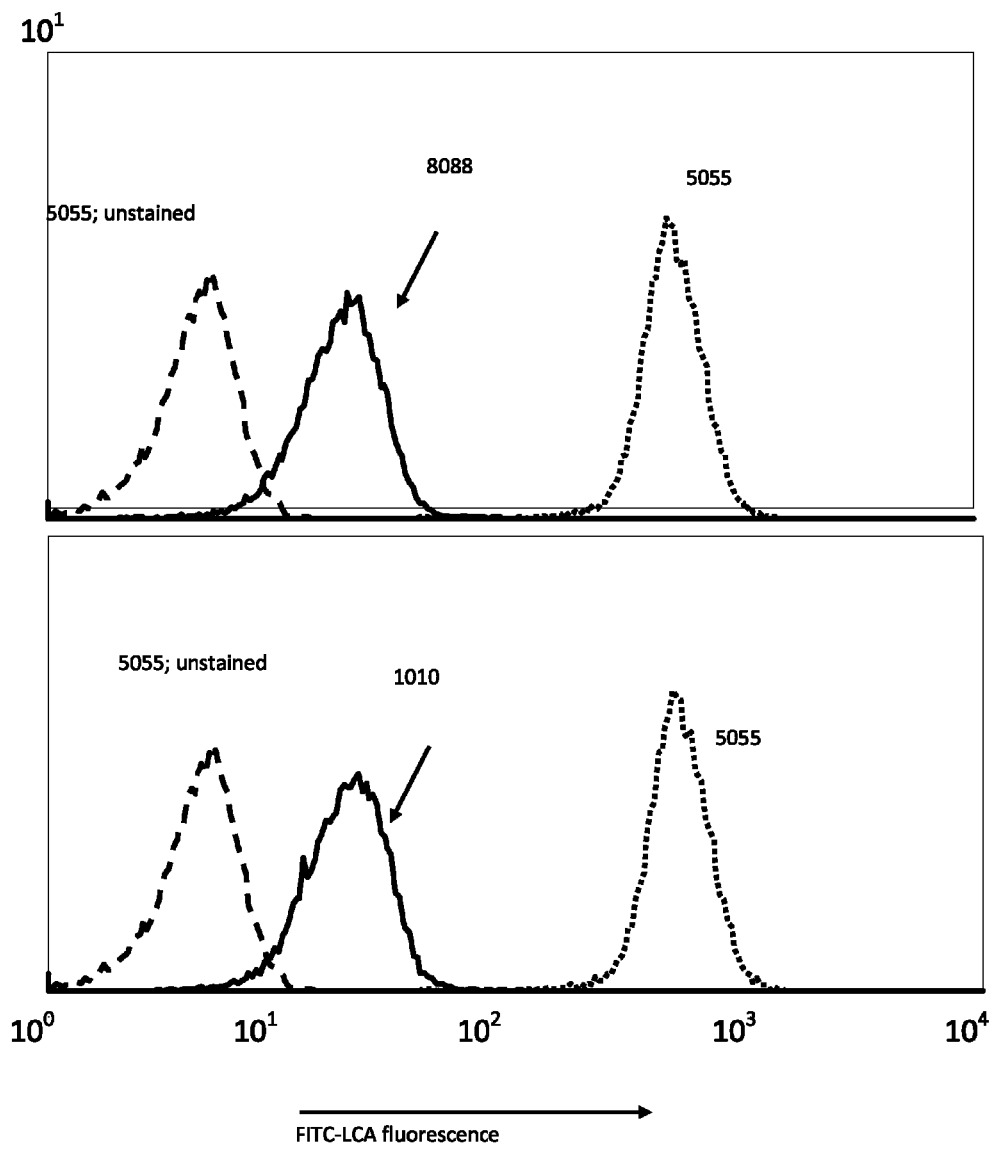
FIG. 4 shows flow cytometry histograms of unstained 5055 cells, and histograms of 5055, 8088, and 1010 cells stained with LCA.

Example 6: Fucosylation in CHO Cell Lines with Two Amino Acid Changes in the FX Gene 8088 and 1010 are two cell lines isolated from 6066 cells without the use of exogenous, recombinant nucleic acid. 6069, 2020, and 2121 are three cell lines isolated from 6066-1 cells without the use of exogenous, recombinant nucleic acid. Sequences of the major transcript for FX gene were determined by RT-PCR (Table 2). These five cell lines were found to have the same L289S mutation in 6066 and 7077 cells. The FX transcripts in all five cell lines also carry mutations that change one amino acid in addition to the L289S change. These mutations are summarized in Table 2. 8088, 1010, 6069, 2020, and 2121 cells exhibited reduced binding to LCA (FIG. 4), suggesting reduced protein fucosylation in these cells.

To examine fucosylation proficiency in 8088 and 1010 cells, Ab 1 was produced from these two host cells by stable transfection. The transfected cultures were selected with 400 micrograms/mL hygromycin for two weeks. Cells that were resistant to hygromycin were adapted to grow in Medium 1 in suspension cultures. Recombinant Ab 1 was produced in three-day shaker flask cultures as well as in twelve-day fed-batch bioreactor cultures. Ab 1 was purified from the conditioned media and the levels of Ab 1 fucosylation were determined by HPLC (Table 2). As shown in Table 2, the transfected 8088 and 1010 cells produced recombinant Ab 1 antibody with fucosylation level between 0.53% and 0.96% in shakers and bioreactors at 34° C.

Fucosylation proficiency in 6069, 2020, 2121 cells was also examined after purification of Ab 1 protein produced in shaker flask cultures. Table 2 shows that these three cell lines produced Ab 1 with fucosylation levels ranging from 0.82% to 0.94%.

TABLE 2

| Host Cell Line Designation | Production Cell Line Designation | FX Mutation | Reporter Protein | Fucosylation in Shaker (%) | Fucosylation in Bioreactor (%) |
|---|---|---|---|---|---|
| 8088 (8088) | 8088-1 | L289S, N90K | Ab 1 | 0.96 | 0.71 |
| 1010 | 1010-1 | L289S, G211R | Ab 1 | 0.94 | 0.53 |
| | 2121 | L289S, P136L | Ab 1 | 0.82 | |
| | 2020 | L289S, IM79S | Ab 1 | 0.94 | |
| | 6069 | L289S, N79S | Ab 1 | 0.87 | |

Example 7: Fucosylation Proficiency in 6066-1 is Temperature-Dependent

Figure 5:
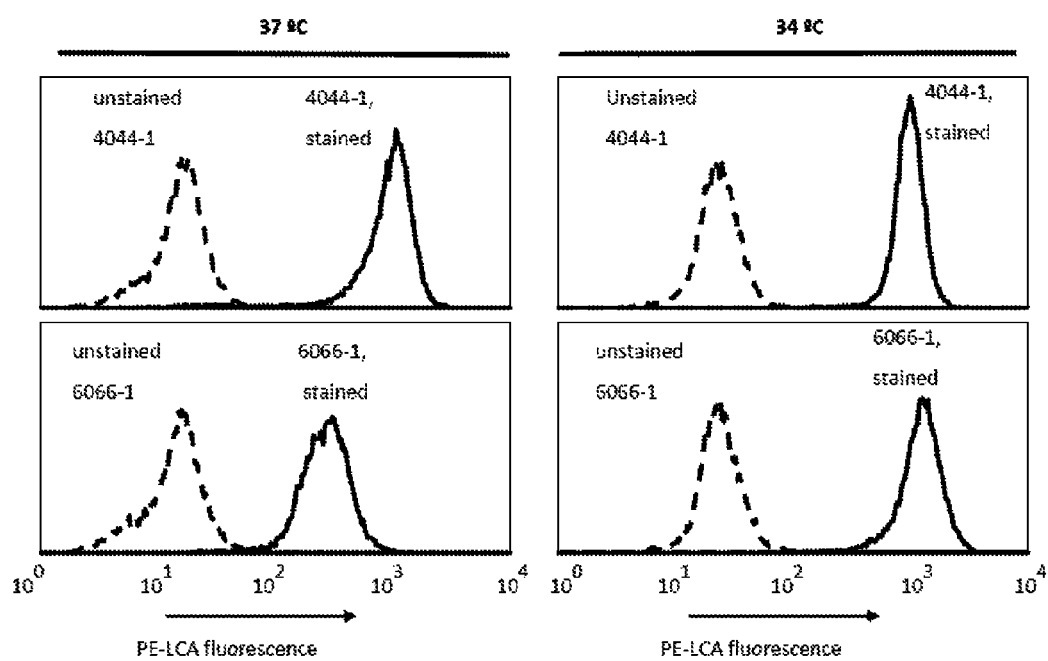
FIG. 5 shows flow cytometry histograms of 4044-1 and 6066-1 cells cultured at 37° C. and 34° C. before and after staining with LCA.

The effect of culture temperatures on protein fucosylation in 6066-1 cells was examined by LCA staining and by analysis of fucosylation of Ab 1 protein produced from these cells. FIG. 5 shows the LCA stains of 4044-1 and 6066-1 cells grown at both 37° C. and 34° C. 4044-1 cells grown at 34° C. and 37° C. were stained similarly by LCA. 6066-1 cells grown at 34° C. bound LCA at a level that was significantly higher than 6066-1 cells grown at 37° C. Table 3 shows the level of fucosylation in Ab 1 protein produced from 4044-1 and 6066-1 cells in shaker flask cultures at 34° C. and 37° C. 4044-1 cells produced AB 1 with 96% and 95% fucosylation when grown at 34° C. and 37° C. respectively. In contrast, 6066-1 cells produced Ab 1 with about 70% and 7% fucosylation at 34° C. and 37° C. respectively. This result indicates that the fucosylation level in 6066-1 cells is temperature-dependent.

TABLE 3

| Production cell line Designation | Consensus FX Mutation | Culture Temp. (° C.) | Fucosylation in Ab 1 (%) |
|---|---|---|---|
| 4044-1 | None | 37 | 95 |
| 4044-1 | None | 34 | 96 |
| 6066-1 | L289S | 37 | 7 |
| 6066-1 | L289S | 34 | 70 |

Example 8: Fucosylation of CHO Cells Cultured in Media Supplemented with L-Fucose In mammalian cells, GDP-fucose can be produced by the de novo synthesis pathway and the salvage pathway (Becker and Lowe (2003) Fucose: biosynthesis and biological function in mammals, Glycobiology, 13(7):41R-53R). In cells grown in culture medium lacking L-fucose, GDP-fucose is produced by GMD and FX proteins from GDP-mannose. In medium with L-fucose. GDP-fucose can be generated from L-fucose by L-fucose kinase and GDP-L-fucose pyrophosphorylase. GDP-fucose produced from either pathway is transported to the Golgi apparatus through GDP-fucose transporter. In the Golgi, the fucosyltransferase protein FUT8 converts glycoprotein into fucosylated proteins with GDP-fucose. Fucosylation proficiency of 6066-2. 8088, and 1010 cells grown in culture media with and without 5 mM L-fucose was examined. 6066-2 cells expressed the Ab 2 antibody and carried the L289S mutation in the FX gene transcripts (Example 2 and Table 1). By HPLC analysis of purified Ab 2, 6066-2 cells grown in shaker flasks produced AB 2 with 1.9% fucosylation in Medium 2 with no added L-fucose. In contrast, 6066-2 cells grown in shaker flasks produced Ab 2 with 93.5% fucosylation in Medium 2 supplemented with 5 mM L-fucose. This result indicates that the salvage pathway for GDP-fucose synthesis, the GDP-fucose transporter, and the FUT8 proteins were functional in 6066-2 cells.

Figure 6:
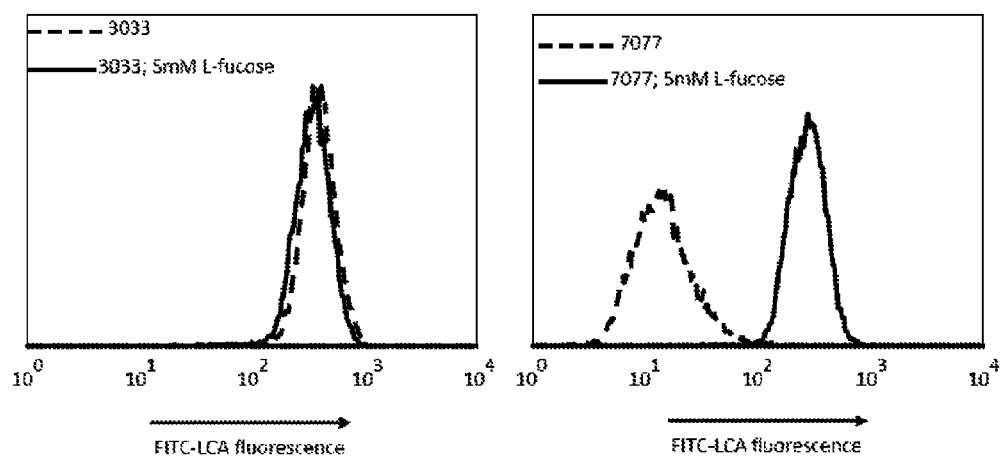
FIG. 6 shows flow cytometry histograms of 3033, 7077, 8088, and 1010 cells cultured in media with and without 5 mM L-fucose, and histograms of 5055 cells cultured in medium without L-fucose. All cells were stained with LCA.
Figure 6:
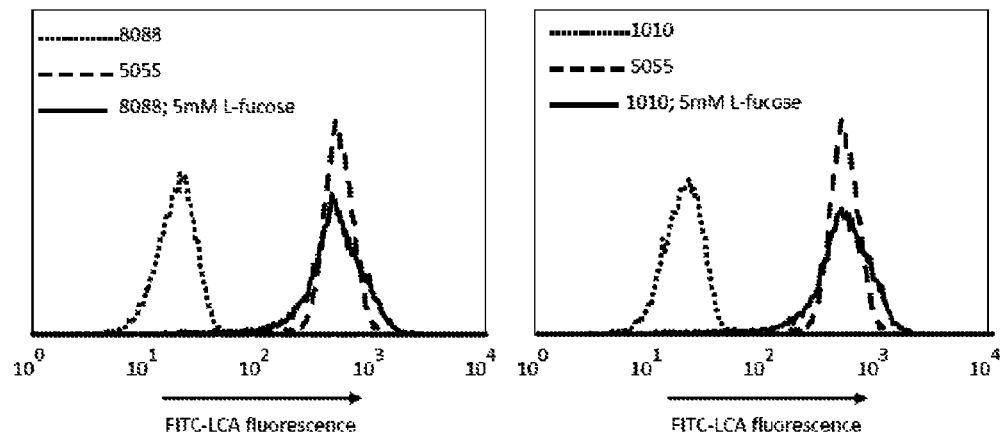

The relative fucosylation proficiencies of 3033, 5055, 7077, 8088, and 8088 cells grown in Medium 2 with and without 5 mM L-fucose were examined by staining with LCA (FIG. 6). 3033 and 5055 cells bound similar levels of LCA with and without L-fucose supplementation. 7077, 8088, and 8088 cells bound significantly more LCA when grown in media with 5 mM L-fucose than in media lacking L-fucose. This result suggests that 7077, 8088, and 8088 cells had functional GDP-fucose transporter and functional FUT8 protein.

Example 9: Fucosylation in 8088 Transfected with FX Gene

Figure 7:
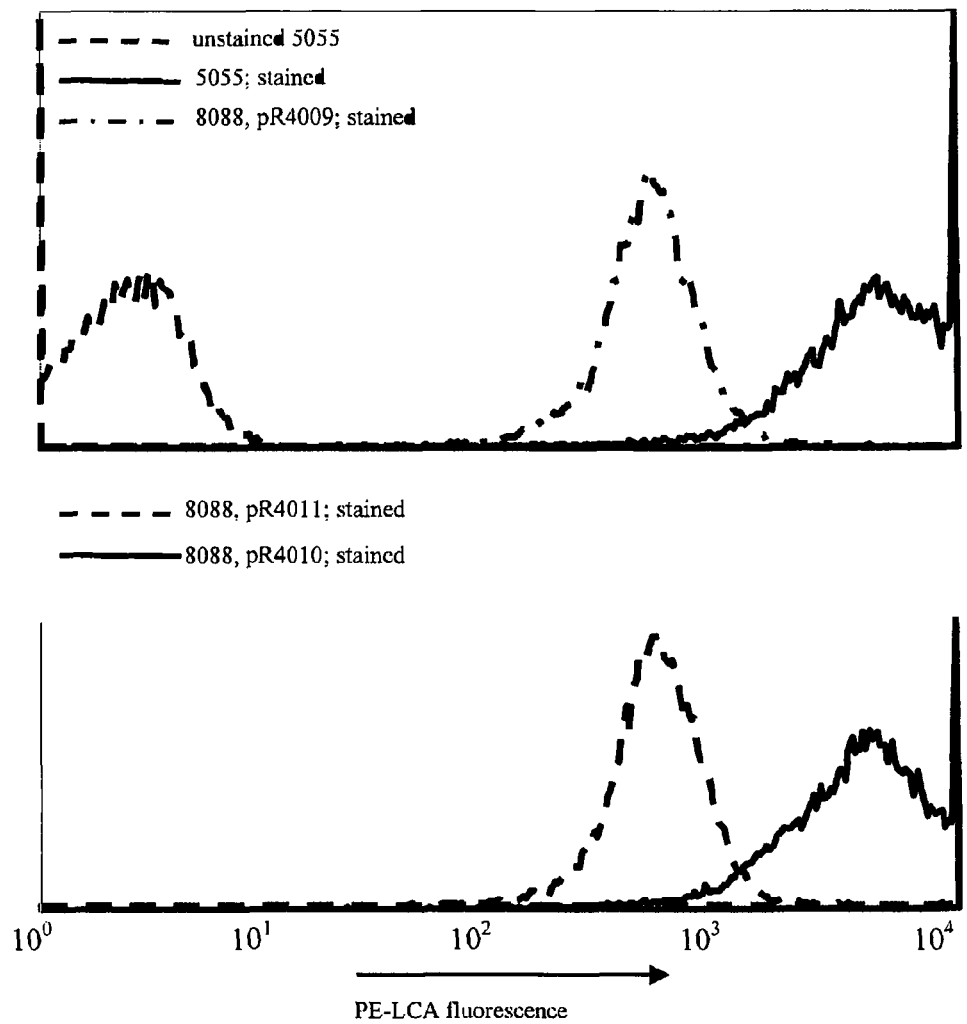
FIG. 7 shows flow cytometry histograms of 8088 cells stably transfected with pR4009, pR4010, and pR4011, and 5055 cells.

To confirm that the reduced fucosylation level seen in 8088 cells was due to the mutant FX gene (with L289S and N90K mutations), wild type FX gene and the mutant FX gene were expressed in 8088 cells by stable transfection and then fucosylation proficiency of the transfected cells was examined by staining the cells with LCA. As a control, 8088 cells were separately transfected with the vector pR4009 (loxed cassette having hygromycin resistance gene and EGFP gene). Vectors pR4010 and pR4011 contain the wild type FX gene and the L289S N90K FX gene placed in between the CMV promoter and the Lox511 site in pR4009, respectively. 8088 cells transfected with pR4004 and either pR4009, pR4010, or pR4011 were selected with 400 micrograms/mL hygromycin for 14 days. The cells that underwent Cre-mediated cassette exchange at EESYR expressed EGFP but not EYFP. The cells that were EGFP-positive but EYFP-negative were isolated by cell sorting. After expansion in tissue culture at 34° C., the sorted cells were sequentially stained with biotin-LCA and PE-streptavidin. 8088 transfected with the vector pR4009 and pR4011 exhibited the same level of LCA staining. In contrast, 8088 cells transfected with pR4010 exhibited a level of LCA staining comparable to 5055 cells (FIG. 7). In summary, wild type FX protein, but not the L289S N90K mutant FX protein, was able to restore the fuscosylation level in 8088 cells as assayed by LCA staining. This result indicates that the lower fucosylation level in 8088 cells was due to the L289S N90K mutation in FX protein in these cells.

Example 10: HPLC and Mass Spectrometry of Glycans: Abs 3.1 and 3.2

Cell line 8088, the CHO line having the FX gene modification that codes for an FX protein substitution L289S and N90K, was separately transfected with plasmids encoding heavy (human IgG1) and light (human kappa) chains of two human antibodies with different variable regions that specifically bind the same growth factor receptor (Antibody 3.1 and Antibody 3.2). Cells expressing each antibody were grown in Medium 2 in the presence and in the absence of 10 mM fucose for 3 days at 37° C., and glycans from the antibodies under each set of conditions were isolated and identified by mass spectroscopy.

Figure 8:
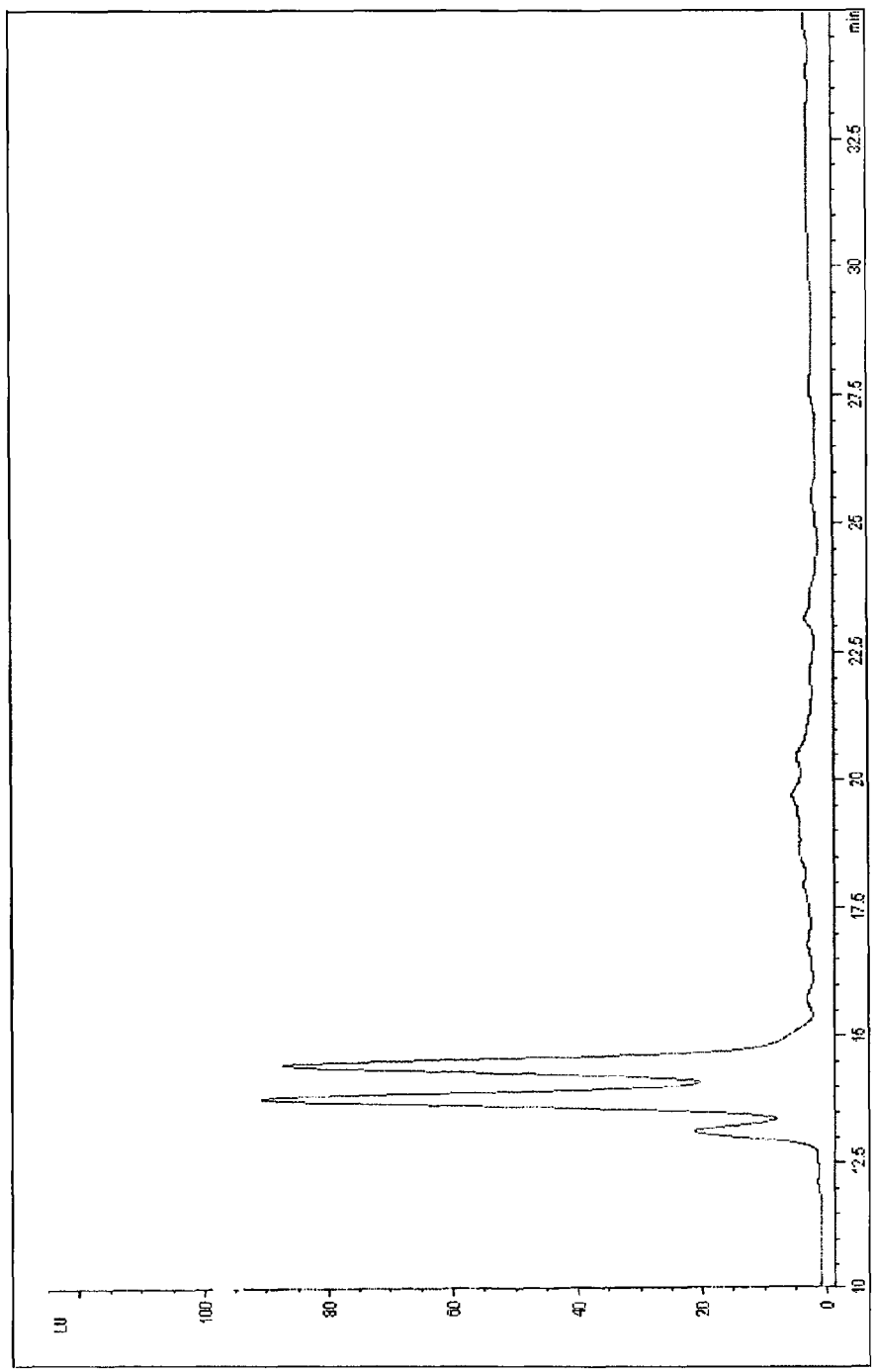
FIG. 8 shows glycan separation by HPLC for Ab 3.1 in 8088 cells grown at 37° C. in the absence of an external fucose source (1.47% fucosylation).
Figure 9:
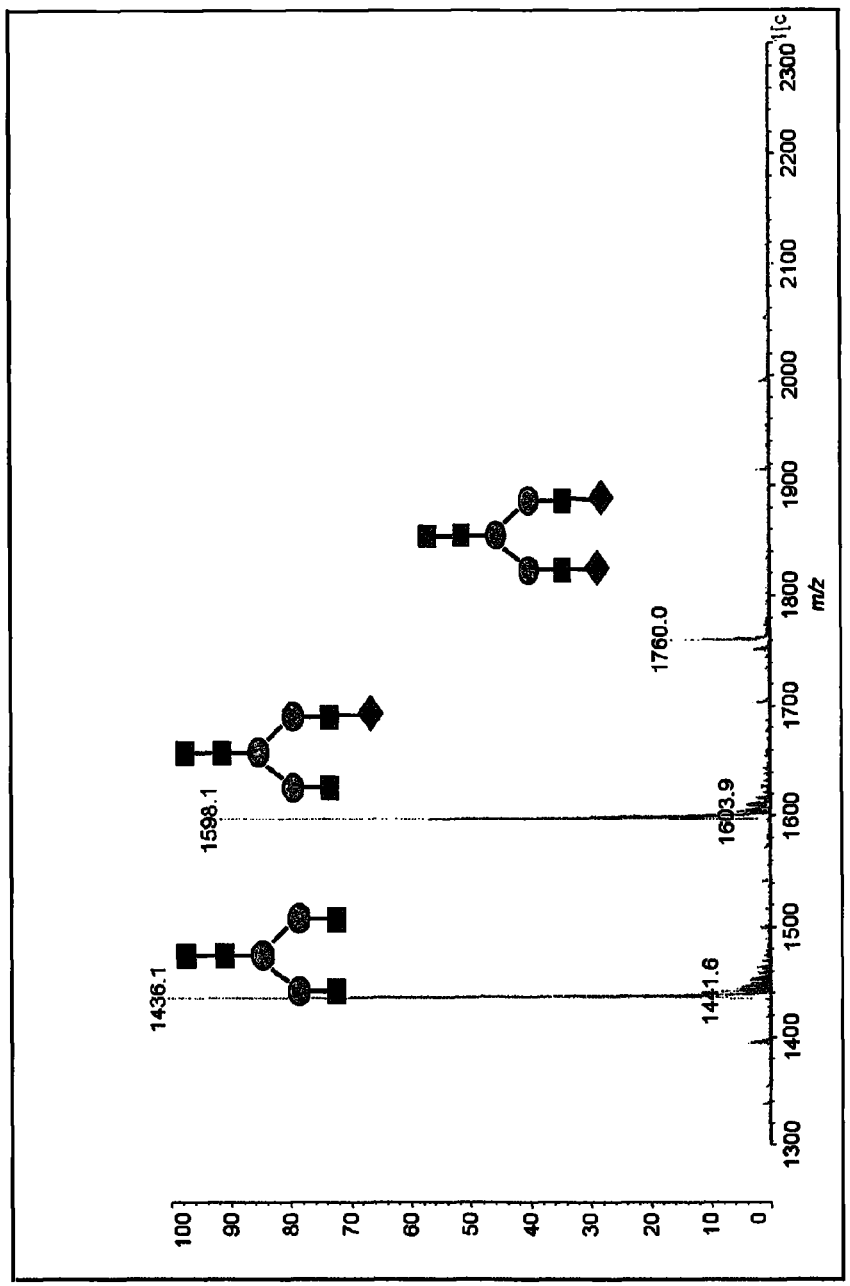
FIG. 9 shows mass spectrometry results for the glycans of FIG. 8; structures of glycans are presented to the right of each peak. GlcNAc residues are represented by squares; mannose residues are represented by circles; galactose residues are represented by diamonds.
Figure 10:
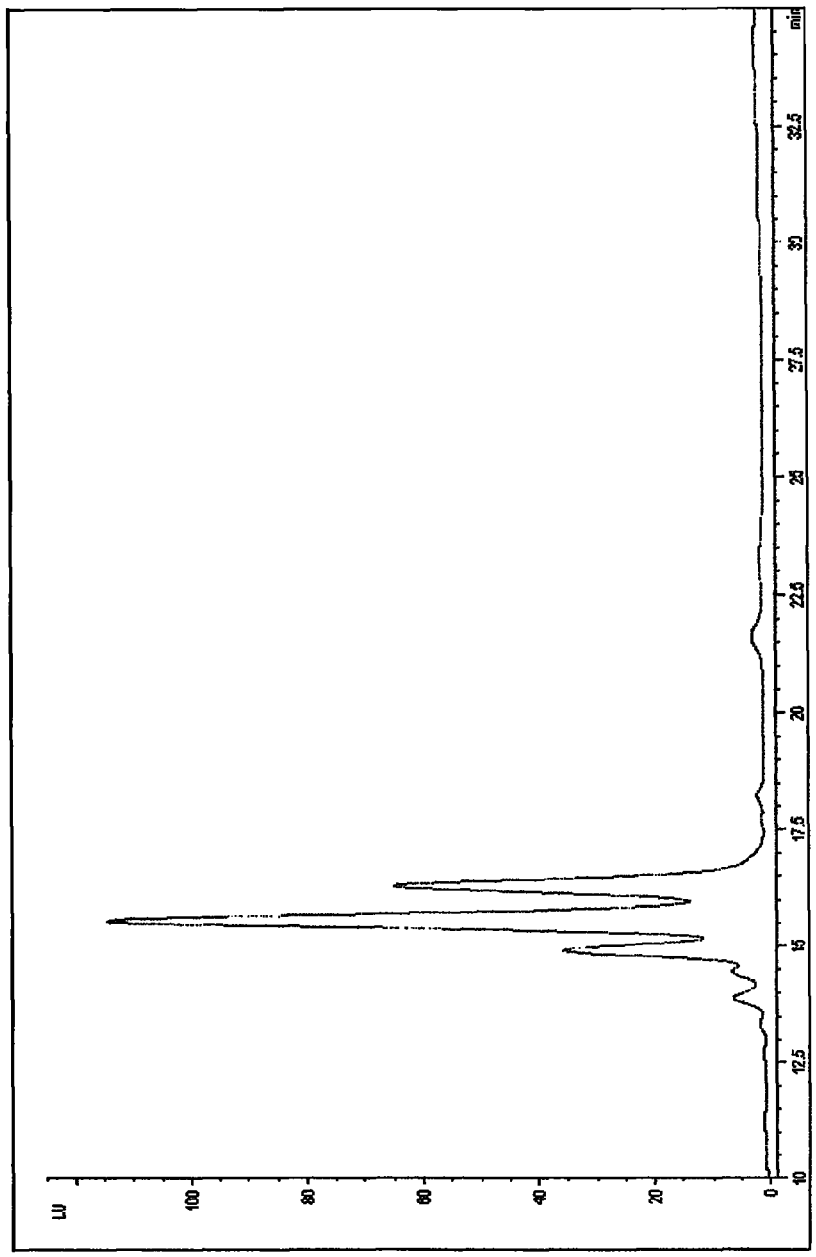
FIG. 10 shows glycan separation by HPLC for Ab 3.1 in 8088 cells grown at 37° C. in the presence of 10 mM fucose (95.22% fucosylation).
Figure 11:
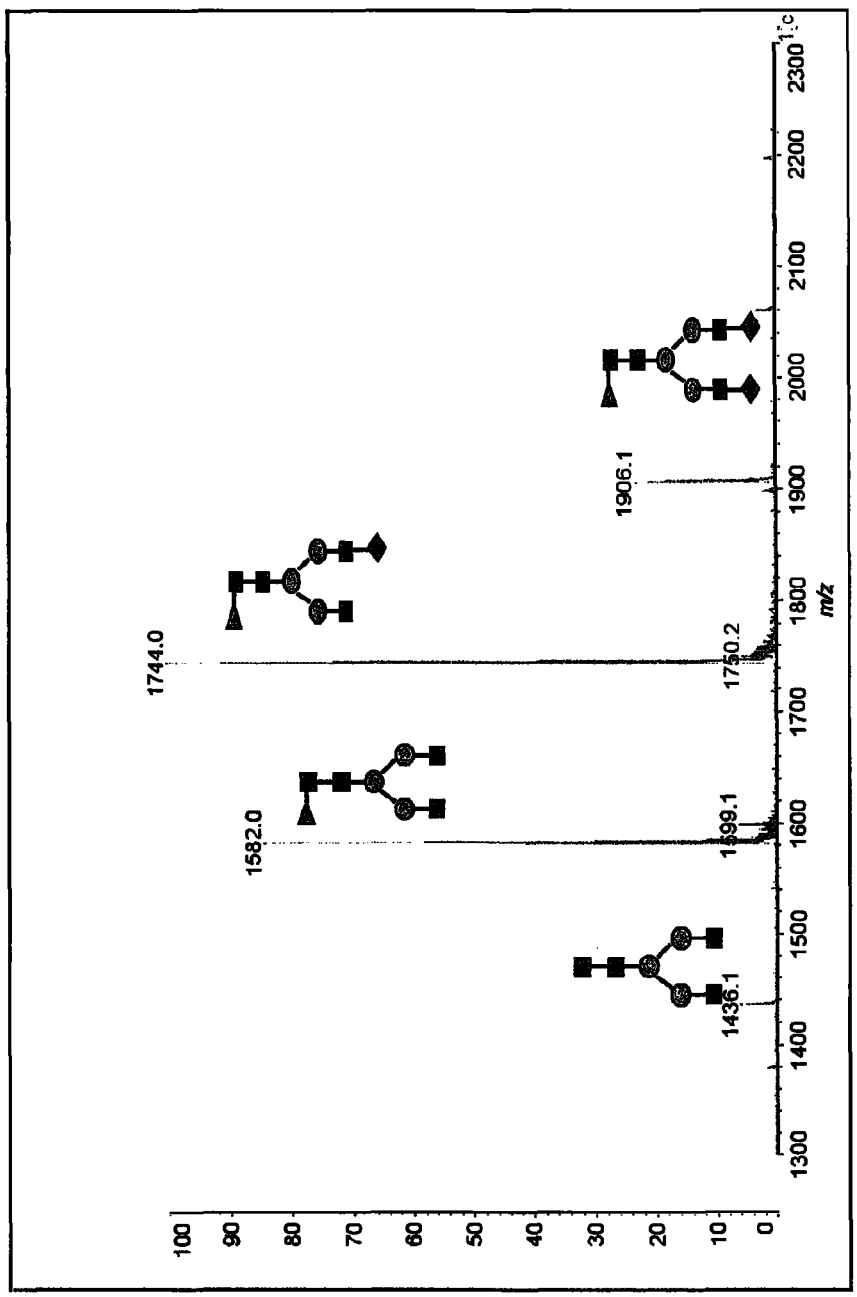
FIG. 11 shows mass spectrometry results for the glycans of FIG. 10; structures of glycans are presented to the right of each peak. GlcNAc residues are represented by squares; mannose residues are represented by circles; galactose residues are represented by diamonds; fucose residues are represented by triangles.

8088 cells expressing A3.1 in the absence of fucose produced three major glycan peaks on HPLC (FIG. 8), representing three different nonfucosylated glycans on a mass spectrum that differed in terminal galactosylation (FIG. 9) with about 1.47% fucosylation. 8088 cells expressing A3.1 in the presence of 10 mM fucose produced three major glycan peaks on HPLC (FIG. 10), representing three different fucosylated glycans and one nonfucosylated glycal on a mass spectrum (FIG. 11), with about 95.22% fucosylation.

Figure 12:
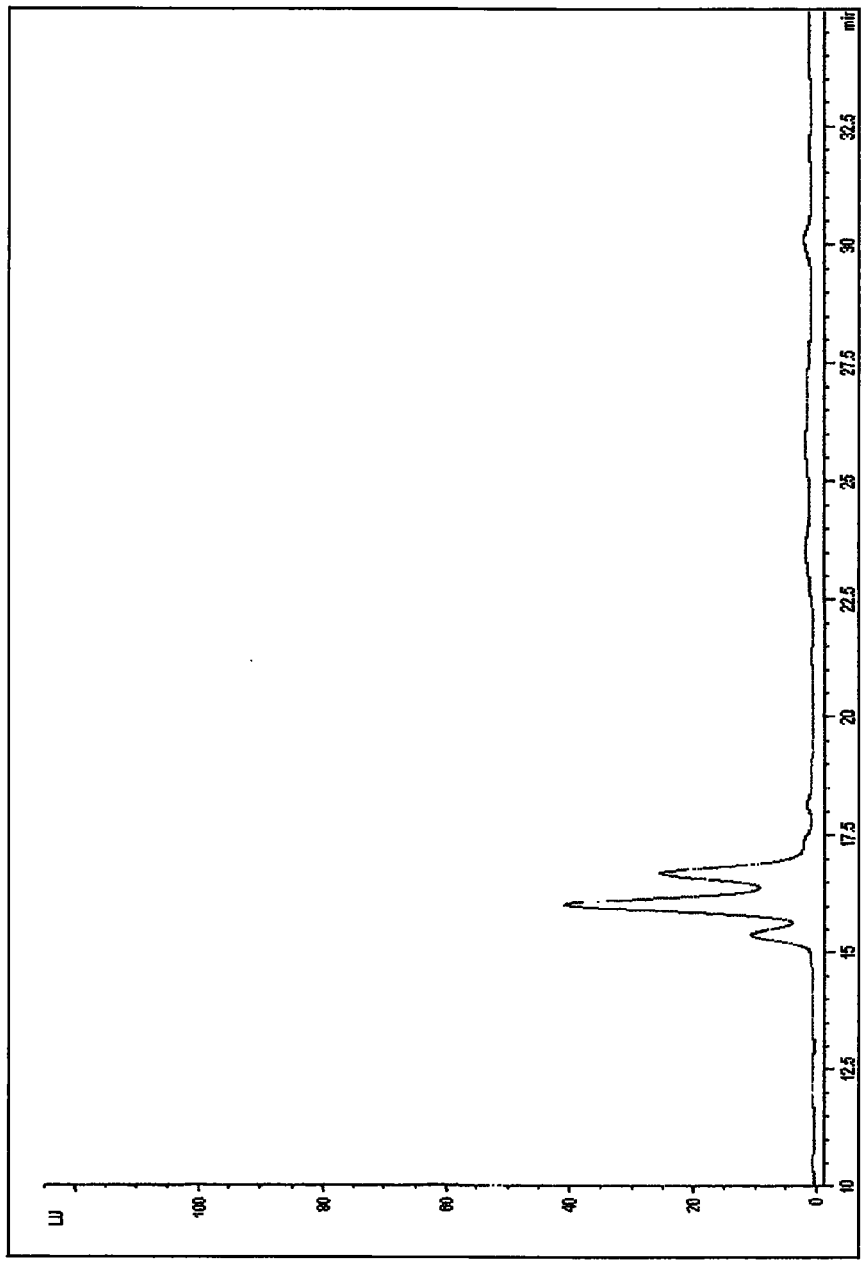
FIG. 12 shows glycan separation by HPLC for Ab 3.2 in 8088 cells grown at 37° C. in the absence of an external fucose source (5.73% fucosylation).
Figure 13:
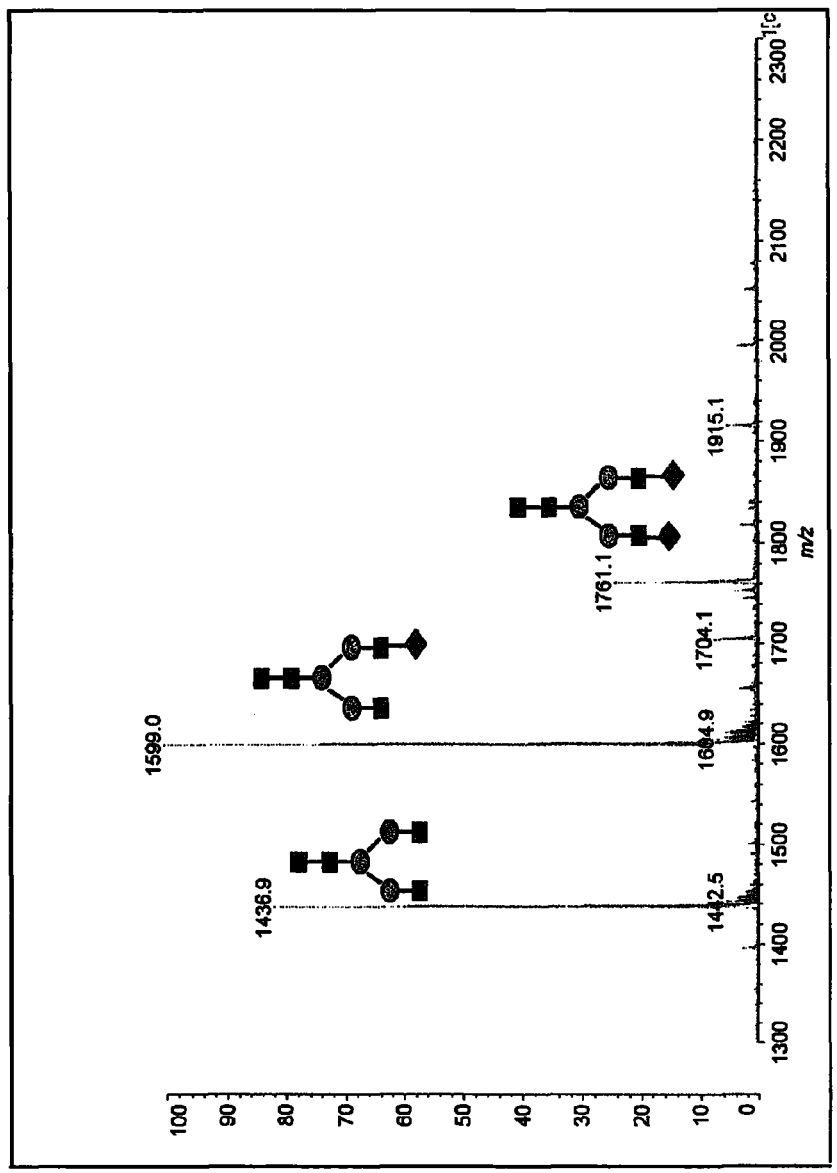
FIG. 13 shows mass spectrometry results for the glycans of FIG. 12; structures of glycans are presented to the right of each peak. GlcNAc residues are represented by squares; mannose residues are represented by circles; galactose residues are represented by diamonds.
Figure 14:
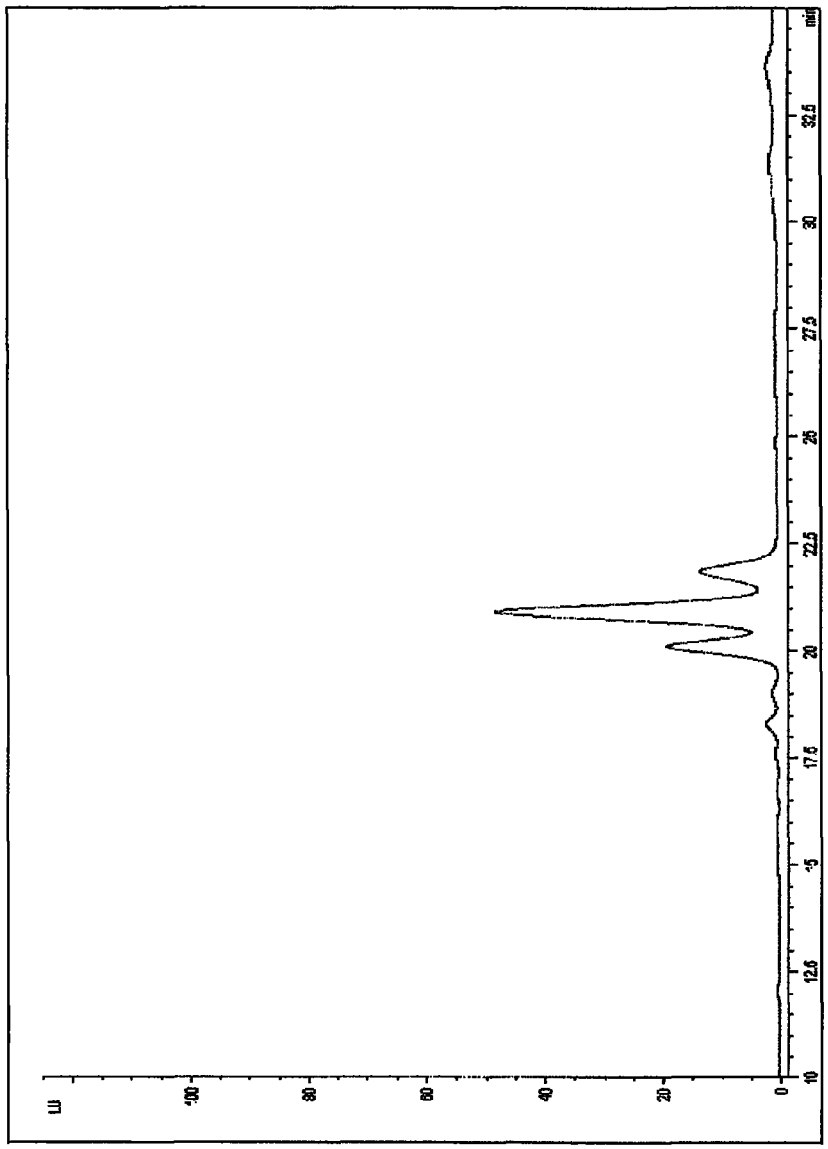
FIG. 14 shows glycan separation by HPLC for Ab 3.2 in 8088 cells grown at 37° C. in the presence of 10 mM fucose (95.63% fucosylation).
Figure 15:
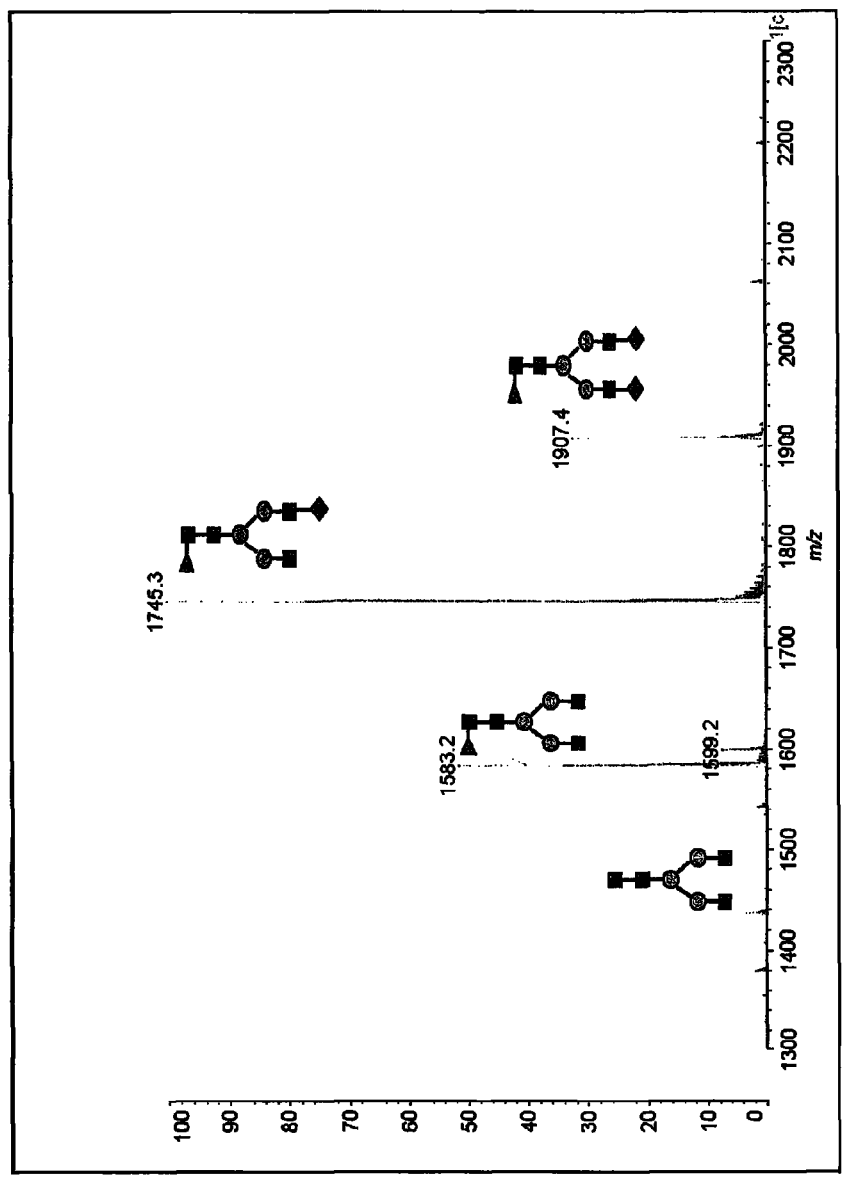
FIG. 15 shows mass spectrometry results for the glycans of FIG. 14; structures of glycans are presented to the right of each peak. GlcNAc residues are represented by squares; mannose residues are represented by circles; galactose residues are represented by diamonds; fucose residues are represented by triangles.

8088 cells expressing A3.2 in the absence of fucose produced three major glycan peaks on HPLC (FIG. 12), representing three different nonfucosylated glycans on a mass spectrum that differed in terminal galactosylation (FIG. 13) with about 5.73% fucosylation. 8088 cells expressing A3.2 in the presence of 10 mM fucose produced three major glycan peaks on HPLC (FIG. 14), representing three different fucosylated glycans and a fourth minor amount of nonfucosylated glycan on a mass spectrum (FIG. 15), with about 95.63% fucosylation.

Results of glycan analysis for fucose-fed and non-fucose fed 8088 cells expressing Antibody 3.1 or Antibody 3.2 are summarized in FIG. 16, grouped according to glycan type. Columns indicating percentage of antibody under a particular condition sum to 100. For Ab 3.1, total fucosylation in the absence of 10 mM fucose was 1.87%; for Ab 3.2, total fucosylation in the absence of 10 mM fucose was 5.73% (sum the corresponding columns in the last three rows of the table of FIG. 16). In the presence of 10 mM fucose, total fucosylation for Ab 3.1 was 95.22%; in the presence of 10 mM fucose total fucosylation for Ab 3.2 was 95.63% (sum the corresponding columns in final three rows of the table of FIG. 16). These data establish that the low fucosylation cell lines fucosylate no more than about 1.87% or 5.73% in the absence of fucose, but that fucosylation can be recovered in the presence of fucose up to at least about 95.22% or 95.63% fucosylation.

For glycan analysis, 100 microgram aliquots of each of the two antibody (Antibody 3.1 and Antibody 3.2) samples were resuspended in 45 microliters of denaturation buffer containing 50 mM Tris (pH 8.0), 2.0 mM tris(2-carboxyethyl)phosphine (TCEP), 0.5% SDS. The protein was denatured by heating at 80° C. for 7 min. The N-linked glycans on the antibody were released following incubation with 10 mU of PNGase F and 1% NP40 at 37° C. overnight. The released glycans were fluorescently labeled by addition of 200 microliters of derivatization solution (30 mg/mL anthranilic acid (AA) and 20 mg/mL sodium cyanoborohydride in methanol containing 4% (w/v) sodium acetate and 2% (w/v) boric acid), and incubation at 80° C. for 1 hour. The AA derivatized glycans were further separated from excess reagents using a solid phase extraction cartridge (Oasis™ HLB cartridge, Waters Corp.) and eluted into 200 microliters of 5% acetonitrile. For HPLC separation of the glycans, a Thermo Hypercarb™ column (3 µm, 100×2.1 mm) was used at a flow rate of 0.15 mL/min. Mobile phase A was 0.05% TFA in $H_2O$, and mobile phase B 0.045% TFA in 90% acetonitrile and 10% $H_2O$. An aliquot of 10 microliters of fluorescent derivatized oligosaccharides was mixed with 90 microliters of 0.1% TFA in $H_2O$ and injected onto the column pre-equilibrated in 25% mobile phase B. Post sample injection, the gradient was increased to 30% B over 5 min, followed by another increase to 43% B over 39 minutes to get the oligosaccharide separated. The AA-labeled glycans were detected using a fluorescence detector with excitation wavelength at 230 nm and emission wavelength at 450 nm. The mass spectrometry analysis of the AA-labeled glycans were conducted using a Shimadzu Axima™ MALDI-TOF system. One hundred microliters of the derivatized glycans were dried in speed vacuum and resuspended in 10 microliters 0.1% TFA. The concentrated glycans were further desalted using Nutip Hypercarb™, and eluted into 30 microliters of 0.1% TFA in 65% acetonitrile, and speed vacuum dried. The lyophilized glycans were redissolved in 2 microliters 10 mg/mL DHB (2,5-dihydroxybenzioc acid) in 70% acetonitrile, and spotted onto the MALDI plate. The spectra were collected under linear negative mode, with post extraction at 1500 mu, and laser power set between 60-90% of maximum power (6 mW) operated at wavelength of 337 nm.

We claim:

1. A cell that comprises a nucleic acid encoding an FX protein, wherein the FX protein comprises an amino acid sequence that is at least 90% identical to SEQ ID NO: 1, and wherein the FX protein comprises a modification relative to SEQ ID NO: 1, the modification comprising a substitution with a serine at position 289.

2. A cell that comprises a nucleic acid encoding an FX protein, wherein the FX protein comprises an amino acid sequence that is at least 90% identical to SEQ ID NO: 1, and wherein the FX protein comprises a modification relative to SEQ ID NO: 1, the modification comprising a substitution with a Serine at position 289 and a substitution with a lysine at position 90.

3. The cell of claim 1, wherein the FX protein comprises an amino acid sequence that is at least 95% identical to SEQ ID NO: 1.

4. The cell of claim 2, wherein the FX protein comprises an amino acid identical to SEQ ID NO: 1 except for having a serine at position 289 and a lysine at position 90.

5. The cell of claim 1, wherein the cell is a Chinese hamster ovary (CHO) cell.

6. The cell of claim 2, wherein the cell is a Chinese hamster ovary (CHO) cell.

7. The cell of claim 1, wherein the cell expresses said FX protein and a glycoprotein.

8. The cell of claim 7, wherein the glycoprotein is an antibody.

9. The cell of claim 7, wherein the ability of the cell to fucosylate said glycoprotein at 37° C. is no more than 10% of the ability to fucosylate the glycoprotein exhibited by a cell lacking said modification.

10. The cell of claim 2, wherein the cell expresses said FX protein and a glycoprotein.

11. The cell of claim 10, wherein the ability of the cell to fucosylate said glycoprotein at 37° C. is no more than 10% of the ability to fucosylate the glycoprotein exhibited by a cell lacking said modification.

12. The cell of claim 10, wherein the glycoprotein is an antibody.

13. A method for making a glycoprotein with reduced fucosylation, the method comprising:
   (a) culturing a cell of claim 1, wherein the cell expresses said FX protein and a glycoprotein; and
   (b) isolating the glycoprotein from said culture.

14. The method of claim 13, wherein said culturing further comprises culturing the cell at a temperature of 37° C. in the absence of an external fucose source.

15. The method of claim 13, wherein the glycoprotein is an antibody.

16. The method of claim 13, wherein no more than 2% of said glycoprotein is fucosylated.

17. A method for making a glycoprotein with reduced fucosylation, the method comprising:
   (a) culturing a cell of claim 2, wherein the cell expresses said FX protein and a glycoprotein; and
   (b) isolating the glycoprotein from said culture.

18. The method of claim 17, wherein said culturing further comprises culturing the cell at a temperature of 37° C. in the absence of an external fucose source.

19. The method of claim 18, wherein the glycoprotein is an antibody.

20. The method of claim 19, wherein no more than 2% of said glycoprotein is fucosylated.

* * * * *